United States Patent [19]

Murphy et al.

[11] Patent Number: 5,225,443

[45] Date of Patent: Jul. 6, 1993

[54] INSECTICIDAL N'-SUBSTITUTED-N'-SUBSTITUTED N,N'-DIACYLHYDRAZINES

[75] Inventors: Raymond A. Murphy; Adam C.-T. Hsu, both of Lansdale, Pa.

[73] Assignee: Rohm and Haas Company, Philadelphia, Pa.

[21] Appl. No.: 726,142

[22] Filed: Jun. 24, 1991

Related U.S. Application Data

[63] Continuation of Ser. No. 274,635, Nov. 15, 1988, abandoned, which is a continuation of Ser. No. 858,482, May 1, 1986, abandoned.

[51] Int. Cl.$^5$ .................... A01N 37/18; C07C 243/24
[52] U.S. Cl. .................... 514/615; 564/149; 564/150
[58] Field of Search ............... 564/149, 150; 514/615

[56] References Cited

U.S. PATENT DOCUMENTS

| | | |
|---|---|---|
| 3,092,660 | 6/1963 | Gutmann et al. . |
| 3,636,112 | 1/1972 | Draber et al. . |
| 3,660,426 | 5/1972 | Cale et al. ................ 564/149 X |
| 3,699,111 | 10/1972 | Kaugars . |
| 3,737,533 | 6/1973 | Moon et al. . |
| 3,745,215 | 7/1973 | Kaugars . |
| 3,746,760 | 7/1973 | Sheppard et al. . |
| 3,748,356 | 7/1973 | Wellinga et al. . |
| 3,786,094 | 1/1974 | Perronnet et al. . |
| 3,809,703 | 5/1974 | Kaugars . |
| 3,821,261 | 6/1974 | Kaugars . |
| 3,824,233 | 7/1974 | Friedman . |
| 3,834,892 | 9/1974 | Moon . |
| 3,867,449 | 2/1975 | Moore . |
| 3,870,505 | 3/1975 | Kaugars . |
| 3,879,542 | 4/1975 | Kaugars . |
| 3,897,559 | 7/1975 | Friedman . |
| 3,932,660 | 1/1976 | Moore . |
| 3,989,842 | 11/1976 | Wellinga et al. . |
| 4,007,165 | 2/1977 | MacLeay et al. . |
| 4,008,217 | 2/1977 | Moon et al. . |
| 4,008,273 | 2/1977 | MacLeay et al. . |
| 4,017,540 | 4/1977 | Kaugars et al. . |
| 4,018,645 | 4/1977 | Takahashi et al. . |
| 4,062,934 | 12/1977 | Tilly et al. ................... 424/5 |
| 4,198,434 | 4/1980 | Bergman et al. . |
| 4,203,932 | 5/1980 | Brown . . |
| 4,258,059 | 3/1981 | Auerbach et al. ............. 424/321 |
| 4,508,734 | 4/1985 | Lang et al. . |
| 4,533,676 | 8/1985 | Sirrenberg et al. . |
| 4,547,524 | 10/1985 | Kaneko et al. . |
| 4,550,204 | 10/1985 | Von Gentzkow et al. ......... 564/134 |
| 4,551,472 | 11/1985 | D'Silva . |
| 4,564,611 | 1/1986 | Stahler et al. ................ 514/99 |

FOREIGN PATENT DOCUMENTS

| | | |
|---|---|---|
| 228564 | 7/1987 | European Pat. Off. . |
| 1668893 | 10/1971 | Fed. Rep. of Germany . |
| 2757584 | 8/1978 | Fed. Rep. of Germany . |
| 1481388 | 7/1977 | United Kingdom . |
| 1573668 | 8/1980 | United Kingdom . |

OTHER PUBLICATIONS

Chemical Abstracts 71:699567 (1969).
Chemical Abstracts 52:11015f (1958).
Chemical Abstracts 51:6529i (1957).
25 Aust. J. Chem., 523–529 (1972).
61 Helv. Chim. Acta, 1477–1510 (1978).
44 J.A.C.S., 2556–2567 (1922).
44 J.A.C.S., 1557–1564 (1972).
48 J.A.C.S., 1030–1035 (1926).
27 Bull. Chem. Soc. Japan, 624–627 (1954).
J. Chem. Soc. (C), 1531–1536 (1966).
56B Chem. Berichte, 954–962 (1923).
590 Annalen der Chemie, 1–36 (1954).
J. Chem. Soc., 4191–4198 (1952).
32 Zhur. Obs. Khim., 2806–2809 (1962).
17 Acta. Chim. Scand., 95–102 (1963).
25 Zhur. Obs. Khim., 1719–1723 (1955).
J. Chem. Soc., 4793–4800 (1964).
36 J. Prakt. Chem., 197–201 (1967).
26 J.O.C., 4336–4340 (1961).
41 J.O.C., 3763–3765 (1976).
94 J.A.C.S., 7406–7416 (1972).
43 J.O.C., 808–815 (1978).
39 J. Econ. Ent., 416–417 (1946).
20 J. Agr. Food Chem., 888–891 (1972).
21 J. Agr. Food Chem., 647–650 (1973).
24 Journal of Medicinal Chemistry, 532–538 (1981).
Friedman, A. et al., "The Photolysis of Benzoyl Chloride (2,4,6-Trichlorophenyl)hydrazone," *Pest. Chem.,*

*Proc. Int. IUPAC Congr. Pest. Chem., 3rd,* 298–301, 1974.
*Chemical Abstracts,* 93:94943e (1980).
*Chemical Abstracts,* 73:3623y (1970).
*Chemical Abstracts,* 96:99275k (1982).
*Chemical Abstracts,* 65:8814a (1966).
*Chemical Abstracts,* 79:122571p (1973).
*Chemical Abstracts,* 77:126648a (1972).
13 *Aldrichimica Acta.,* 33–40 (1980).
8 *J. Pharm. Sci. U.A.R.,* 181–186 (1967).
23 *J. Agric. Food Chem.,* 1084–1088 (1975).
48 *J. Org. Chem.,* 2287–2289 (1983).
92 *Bull. Soc. Chim. Belg.,* 229–232 (1983).
48 *Canadian Journal of Chemistry,* 81–88 (1970).
Bentley, T. et al., "Aspects of Mass Spectra of Organic Compounds, Part XI. Rearrangements in Benzoylhydrazines," *J. Chem. Soc., Perkin I,* 449–453 (1973).
40 *J. Org. Chem.,* 19–24 (1975).
44 *J. Org. Chem.,* 2957–2961 (1979).
46 *J. Org. Chem.,* 83–89 (1980).
Marchetti, L., "Reaction of Cyclohexanone Enamines with Diacyldi-imides," *J. Chem. Soc. Perkin II,* 382–390 (1978).
51 *Can. J. Chem.,* 1587–1597 (1973).
20 *J. Agr. Food. Chem.,* 1187–1190 (1972).
*Chemical Abstracts,* 77:34128c (1972).
28 *Aust. J. Chem.,* 133–141 (1975).
88 J.A.C.S., 4677–4681 (1966).
*Chemical Patents Index Country Alerting Bulletin,* Section C:AGDOC Week 8539, Derwent Publications Ltd., (1985) p. 3.

*Primary Examiner*—Carolyn E. Elmore
*Assistant Examiner*—Shailendra Kumar
*Attorney, Agent, or Firm*—Terry B. Morris

[57] ABSTRACT

This invention relates to insecticidal compositions containing N-substituted-N'-substituted-N,N'-diacylhydrazines methods of using such compositions and novel insecticidal N-substituted-N'-substituted-N,N'-diacylhydrazines.

29 Claims, No Drawings

INSECTICIDAL N'-SUBSTITUTED-N'-SUBSTITUTED N,N'-DIACYLHYDRAZINES

This application is a continuation of application Ser. No. 274,635, filed Nov. 15, 1988, abandoned, which is a continuation of application Ser. No. 858,482, filed May 1, 1986, now abandoned.

BACKGROUND OF THE INVENTION

This invention relates to N-substituted-N'-substituted-N,N'-diacylhydrazines which are useful as insecticides, compositions containing those compounds and methods of their use.

The search for compounds which have a combination of excellent insecticidal activity and low undesirable toxicity is a continuing one because of factors such as the desire for compounds exhibiting greater activity, better selectivity, low undesirable environmental impact, low production cost and effectiveness against insects resistant to many known insecticides.

Compounds of the present invention are particularly suitable for controlling plant-destructive insects in crops of cultivated plants, ornamentals and forestry.

Certain hydrazine derivatives have been disclosed in the literature.

In 25 *Aust. J. Chem.*, 523–529 (1972), several N,N'-dibenzoylhydrazine derivatives are disclosed in which one or both nitrogen atoms are alkylated or phenylated. No biological activity is disclosed for those compounds.

In 61 *Helv. Chim. Acta*, 1477–1510 (1978), several N,N'-dibenzoylhydrazine derivatives are disclosed. No biological activity is disclosed for those compounds.

In 44 *J.A.C.S.*, 2556–2567 (1922), isopropyl hydrazine (CH₃)₂CH-NH-NH₂, symmetrical diisopropyl hydrazine, dibenzoylisopropyl hydrazine and certain derivatives are disclosed. No biological activity is disclosed for those compounds.

In 44 *J.A.C.S.*, 1557–1564 (1972), isopropyl, menthyl and bornyl semicarbazides are disclosed. No biological activity is disclosed for those compounds.

In 48 *J.A.C.S.*, 1030–1035 (1926), symmetrical dimethylphenylmethyl hydrazine and certain related compounds including 1,2-bis-methylphenylmethyl-4-phenylsemicarbazide are disclosed. No biological activity is disclosed for those compounds.

In 27 *Bull. Chem. Soc. Japan*, 624–627 (1954), certain hydrazine derivatives including alpha, beta-dibenzoyl-phenyl hydrazine are disclosed. No biological activity is disclosed for those compounds.

In *J. Chem. Soc.* (C), 1531–1536 (1966), N,N'-dibenzoylphenyl hydrazine and N-acetyl-N'-benzoyl-p-nitrophenyl hydrazine are disclosed. No biological activity is disclosed for those compounds.

In 56B *Chem. Berichte*, 954–962 (1923), symmetrical di-isopropyl hydrazines, symmetrical diisobutyl and certain derivatives including N,N'-diisobutyldibenzoyl hydrazine are disclosed. No biological activity is disclosed for those compounds.

In 590 *Annalen der Chemie*, 1–36 (1954), certain N,N'-dibenzoyl hydrazine derivatives are disclosed including N'-methyl- and N'-(2-phenyl)-isopropyl-N,N'-dibenzoyl hydrazine. No biological activity is disclosed for those compounds.

In *J. Chem. Soc.*, 4191–4198 (1952), N,N'-di-n-propyl hydrazine and the bis-3,5-dinitrobenzoyl derivatives are disclosed. No biological activity is disclosed for those compounds.

In 32 *Zhur. Obs. Khim.*, 2806–2809 (1962), N'-2,4-methyl-2,4-pentadiene-N,N'-dibenzoyl hydrazine is disclosed. No biological activity is disclosed.

In 17 *Acta. Chim. Scand.*, 95–102 (1963), 2-benzoyl-thiobenzhydrazide (C₆H₅—CS—NHNH—CO—C₆H₅) and certain hydrazone and hydrazine derivatives are disclosed including 1,2-dibenzoyl-benzyl hydrazine. No biological activity is disclosed for those compounds.

In 25 *Zhur. Obs. Khim*, 1719–1723 (1955), N,N'-bis-cyclohexyl hydrazine and N,N'-dibenzoylcyclohexyl hydrazine are disclosed. No biological activity is disclosed for those compounds.

In *J. Chem. Soc.*, 4793–4800 (1964), certain dibenzoyl hydrazine derivatives are disclosed including tribenzoyl hydrazine and N,N'-dibenzoylcyclohexyl hydrazine. No biological activity is disclosed for those compounds.

In 36 *J. Prakt. Chem.*, 197–201 (1967), certain dibenzoyl hydrazine derivatives including N'-ethyl-; N'-n-propyl; N'-isobutyl-; N'-neopentyl-; N'-n-heptyl-; and N'-cyclohexylmethyl-N,N'dibenzoyl hydrazines are disclosed. No biological activity is disclosed for those compounds.

In 26 *J.O.C.*, 4336–4340 (1961), N'-t-butyl-N,N'-di-(t-butoxycarbonyl)hydrazide is disclosed. No biological activity is disclosed.

In 41 *J.O.C.*, 3763–3765 (1976), N'-t-butyl-N-(phenylmethoxycarbonyl)-N'-(chlorocarbonyl)hydrazide is disclosed. No biological activity is disclosed.

In 94 *J.A.C.S.*, 7406–7416 (1972), N'-t-butyl-N,N'-dimethoxycarbonylhydrazide is disclosed. No biological activity is disclosed.

In 43 *J.O.C.*, 808–815 (1978), N'-t-butyl-N-ethoxycarbonyl-N'-phenylaminocarbonylhydrazide and N'-t-butyl-N-ethoxycarbonyl-N'-methylaminocarbonylhydrazide are disclosed. No biological activity is disclosed for those compounds.

In 39 *J. Econ. Ent.*, 416–417 (1946), certain N-phenyl-N'-acylhydrazines are disclosed and evaluated for their toxicity against coding moth larvae.

The N-substituted-N'-substituted-N,N'-diacyl hydrazines of the present invention differ from known compounds primarily by their N- and N'-substituents.

Compounds of the present invention are also distinguished by their excellent insecticidal activity against insects of the orders Lepidoptera and Coleoptera and particularly against insects of the order Lepidoptera, without material adverse impact on beneficial insects.

SUMMARY OF THE INVENTION

In accordance with the present invention, there are provided insecticidal compositions and methods of using such compositions wherein the compositions comprise an agronomically acceptable carrier and an insecticidally effective amount of a compound having the formula:

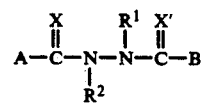

wherein
X and X' are the same or different O, S or NR;
R¹ is unsubstituted (C₄–C₁₀) alkyl including a tertiary carbon atom or a (C₁–C₄) straight chain alkyl substituted with one or two of the same or different $(C_3-C_6)$cycloalkyl;

$R^2$ is $(C_1-C_6)$alkyl; $(C_1-C_6)$alkoxyalkyl having independently the stated number of carbon atoms in each alkyl group; $(C_1-C_6)$alkylthioalkyl having independently the stated number of carbon atoms in each alkyl group; $(C_2-C_6)$alkenyl; $(C_2-C_6)$alkynyl; or phen$(C_1-C_4)$alkyl where the phenyl ring is unsubstituted or substituted with one to three of the same or different halo, cyano, nitro, hydroxy, $(C_1-C_4)$alkyl, $(C_1-C_4)$haloalkyl, $(C_1-C_4)$alkoxy, $(C_1-C_4)$haloalkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; and A and B are the same or different unsubstituted naphthyl or substituted naphthyl where the substituents can be from one to five of the same or different halo; cyano; nitro; hydroxy; $(C_1-C_4)$alkoxy; $(C_1-C_4)$alkyl; carboxy; $(C_1-C_4)$alkoxycarbonyl; $(C_1-C_4)$alkanoyloxy; amino; $(C_1-C_4)$alkylamino; or $(C_1-C_4)$dialkylamino having independently the stated number of carbon atoms in each alkyl group; or unsubstituted phenyl or substituted phenyl where the substituents can be from one to five of the same or different halo; nitroso; nitro; cyano; hydroxy; $(C_1-C_6)$alkyl; $(C_1-C_6)$haloalkyl; $(C_1-C_6)$cyanoalkyl; $(C_1-C_6)$alkoxy; $(C_1-C_6)$haloalkoxy; $(C_1-C_6)$alkoxyalkyl having independently the stated number of carbon atoms in each alkyl group; $(C_1-C_6)$alkoxyalkoxy having independently the stated number of carbon atoms in each alkyl group; $(C_1-C_6)$alkoxycarbonyloxy; carboxyoxy $(C_2-C_6)$alkenyl optionally substituted with halo, cyano, $(C_1-C_4)$alkyl, $(C_1-C_4)$alkoxy, $(C_1-C_4)$haloalkoxy or $(C_1-C_4)$alkylthio; $(C_2-C_6)$alkenylcarbonyl; $(C_3-C_6)$alkadienyl; $(C_2-C_6)$alkynyl optionally substituted with halo, cyano, nitro, hydroxy, $(C_1-C_4)$alkyl, $(C_1-C_4)$alkoxy, $(C_1-C_4)$haloalkoxy or $(C_1-C_4)$alkylthio; $(C_2-C_6)$alkynylcarbonyl; carboxy; $(C_1-C_6)$alkoxycarbonylalkyl; $(C_1-C_6)$alkoxycarboxyalkyl having independently the stated number of carbon atoms in each alkyl group; —COR; $(C_1-C_6)$haloalkylcarbonyl; $(C_1-C_6)$cyanoalkylcarbonyl; $(C_1-C_6)$nitroalkylcarbonyl; $(C_1-C_6)$alkoxycarbonyl; $(C_1-C_6)$haloalkoxycarbonyl; $(C_1-C_6)$alkanoyloxy; amino, $(C_1-C_6)$alkylamino and $(C_1-C_6)$dialkylamino having independently the stated number of carbon atoms in each alkyl group; amino, $(C_1-C_6)$alkylamino or $(C_1-C_6)$dialkylamino having independently the stated number of carbon atoms in each alkyl group substituted with hydroxy, $(C_1-C_4)$alkoxy or $(C_1-C_4)$alkylthio groups; phenylamino; diphenylamino; —CONRR'; —OCONRR'; —C(NR)NR'R"; —N=NR; phenylazo; —NRCOR'; —NRCO$_2$R'; —N(COR)COR'; —OCONRCOR'; sulfhydryl; halothio; thiocyanato; $(C_1-C_6)$alkylthio; $(C_1-C_6)$haloalkylthio; $(C_1-C_6)$alkylsulfinyl; $(C_1-C_6)$alkylsulfonyl; phenyl sulfonyl; $(C_1-C_6)$alkyl sulfonate; $(C_1-C_6)$haloalkylsulfonyloxy; —SO$_2$NRR'; —NRSOR'; —NRSO$_2$R'; —CSR; —CS$_2$R; —NRCSR'; SCOR; $(C_1-C_6)$-trialkylsilyl having independently the stated number of carbon atoms in each alkyl group; unsubstituted phenyl; substituted phenyl having one to three of the same or different halo, cyano, nitro, hydroxy $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; phenoxy where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; benzoyl where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; phenoxycarbonyl where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; phenylthio where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; —CR=N—$R^3$ where $R^3$ is hydroxy, $(C_1-C_4)$alkyl, $(C_1-C_4)$alkoxy, amino, $(C_1-C_4)$alkylamino, $(C_1-C_4)$dialkylamino having independently the stated number of carbon atoms in each alkyl group, phenylamino, —COR, carboxy, $(C_1-C_4)$alkoxycarbonyl, $(C_1-C_4)$alkanoyloxy, benzoyl, phenoxycarbonyl or —CONRR'; or when two adjacent positions on the phenyl ring are substituted with alkoxy groups, these groups may be joined to form a 5 or 6 membered dioxolano or dioxano heterocyclic ring;

where R, R' and R" are hydrogen or $(C_1-C_6)$alkyl; and agronomically acceptable salts thereof.

Also, in accordance with the present invention, there are provided insecticidal compounds of Formula I as described and defined above.

Further, in accordance with the present invention, there are provided methods of using these compounds and compositions.

DETAILED DESCRIPTION OF THE INVENTION

The term "halo" should be understood as including chloro, fluoro, bromo and iodo. The term "alkyl" by itself or as a part of another substituent, unless otherwise stated, includes straight or branched chain groups such as methyl, ethyl, n-propyl, isopropyl, n-butyl, t-butyl, isobutyl, neopentyl and the like and where indicated higher homologues and isomers such as n-octyl, isooctyl and the like. The term "haloalkyl" by itself or as part of another substituent is an alkyl group of the stated number of carbon atoms having one or more halo atoms bonded thereto such as chloromethyl, 1- or 2-bromoethyl, trifluoromethyl and the like. Analogously, "cyanoalkyl" by itself or as part of another group is an alkyl group of the stated number of carbon atoms having one or more cyano groups bonded thereto; "haloalkoxy" by itself or as part of another group is an alkoxy group of the stated number of carbon atoms having one or more halo atoms bonded thereto such as difluoromethoxy, trifluoromethoxy, 2-fluoroethoxy, 2,2,2-trifluoroethoxy and the like. "Alkenyl" and "alkynyl" by themselves or as part of another substituent comprise straight and branched chain groups of the stated number of carbon atoms. "Alkdienyl" is a straight or branched chain alkenyl group comprising two carbon-carbon double bonds that can be conjugated such as 1,3-butadienyl, cumulated such as 1,2-propadienyl or isolated such as 1,4-pentadienyl.

Typical compounds within the scope of the present invention include, but are not limited to:

N-methyl-N'-t-butyl-N,N'-bis(4-chlorobenzoyl)hydrazine
N-methyl-N'-t-butyl-N,N'-bis(3-chlorobenzoyl)hydrazine
N-methyl-N'-t-butyl-N,N'-dibenzoylhydrazine
N-methyl-N'-t-butyl-N,N'-bis(3,4-dichlorobenzoyl)hydrazine
N-methyl-N'-t-butyl-N,N'-bis(4-toluoyl)hydrazine
N-methyl-N'-t-butyl-N,N'-bis(4-nitrobenzoyl)hydrazine
N-methyl-N'-t-butyl-N,N'-bis(4-anisoyl)hydrazine
N-methyl-N'-t-butyl-N,N'-bis(3-nitrobenzoyl)hydrazine
N-methyl-N'-t-butyl-N,N'-bis(3-anisoyl)hydrazine
N-methyl-N'-t-butyl-N,N'-bis(2-nitrobenzoyl)hydrazine
N-methyl-N'-t-butyl-N,N'-bis(2-chlorobenzoyl)hydrazine
N-methyl-N'-t-butyl-N,N'-bis(2-anisoyl)hydrazine
N-methyl-N'-t-butyl-N-(4-toluoyl)-N'-benzoylhydrazine
N-methyl-N'-t-butyl-N,N'-bis(4-cyanobenzoyl)hydrazine
N-methyl-N'-t-butyl-N-(4-toluoyl)-N'-(4-chlorobenzoyl)hydrazine
N-methyl-N'-t-butyl-N-benzoyl-N'-(4-chlorobenzoyl)hydrazine
N-methyl-N'-t-butyl-N-benzoyl-N'-(3-chlorobenzoyl)hydrazine
N-methyl-N'-t-butyl-N-benzoyl-N'-(2-chlorobenzoyl)hydrazine
N-methyl-N'-t-butyl-N,N'-bis(3-toluoyl)hydrazine
N-methyl-N'-t-butyl-N,N'-bis(2-toluoyl)hydrazine
N-methyl-N'-t-butyl-N-benzoyl-N'-(4-toluoyl)hydrazine
N-methyl-N'-t-butyl-N-benzoyl-N'-(3-toluoyl)hydrazine
N-methyl-N'-t-butyl-N-benzoyl-N'-(2-toluoyl)hydrazine
N-methyl-N'-t-butyl-N-benzoyl-N'-(4-anisoyl)hydrazine
N-methyl-N'-t-butyl-N-benzoyl-N'-(3-anisoyl)hydrazine
N-methyl-N'-t-butyl-N-benzoyl-N'-(2-anisoyl)hydrazine
N-methyl-N'-t-butyl-N-benzoyl-N'-(4-n-butylbenzoyl)hydrazine
N-methyl-N'-t-butyl-N-benzoyl-N'-(4-cyanobenzoyl)hydrazine
N-methyl-N'-t-butyl-N-benzoyl-N'-(4-nitrobenzoyl)hydrazine
N-methyl-N'-t-butyl-N-benzoyl-N'-(3-nitrobenzoyl)hydrazine
N-methyl-N'-t-butyl-N-benzoyl-N'-(2-nitrobenzoyl)hydrazine
N-methyl-N'-t-butyl-N,N'-bis(4-t-butylbenzoyl)hydrazine
N-methyl-N'-t-butyl-N-(4-toluoyl)-N'-(3,4-dichlorobenzoyl)hydrazine
N-methyl-N'-t-butyl-N-benzoyl-N'-(4-fluorobenzoyl)hydrazine
N-methyl-N'-t-butyl-N-benzoyl-N'-(3-fluorobenzoyl)hydrazine
N-methyl-N'-t-butyl-N-benzoyl-N'-(2-fluorobenzoyl)hydrazine
N-methyl-N'-t-butyl-N-benzoyl-N'-(2,4-dichlorobenzoyl)hydrazine
N-methyl-N'-isopropyl-N,N'-dibenzoylhydrazine
N-methyl-N'-t-butyl-N-benzoyl-N'-(4-trifluoromethylbenzoyl)hydrazine
N-methyl-N'-t-butyl-N-benzoyl-N'-(3trifluoromethylbenzoyl)hydrazine
N-methyl-N'-t-butyl-N-benzoyl-N'-(2-trifluoromethylbenzoyl)hydrazine
N-methyl-N'-t-butyl-N-benzoyl-N'-(2,5-difluorobenzoyl)hydrazine
N-methyl-N'-(2,2-dimethylethyl)-N,N'-dibenzoylhydrazine
N-methyl-N'-t-butyl-N-benzoyl-N'-(3-cyanobenzoyl)hydrazine
N-methyl-N'-(1-methylpropyl)-N,N'-dibenzoylhydrazine
N-methyl-N'-t-butyl-N-benzoyl-N'-(2,6-difluorobenzoyl)hydrazine
N-methyl-N'-t-butyl-N-(4-chlorobenzoyl)-N'-benzoylhydrazine
N-methyl-N'-t-butyl-N-benzoyl-N'-(3,4-dichlorobenzoyl)hydrazine
N-methyl-N'-t-butyl-N-benzoyl-N'-(3,5-dichlorobenzoyl)hydrazine
N-methyl-N'-t-butyl-N-benzoyl-N'-(2,6-dichlorobenzoyl)hydrazine
N-methyl-N'-t-butyl-N-(4-t-butylbenzoyl)-N'-benzoylhydrazine
N-methyl-N'-t-butyl-N-(2-chlorobenzoyl)-N'-benzoylhydrazine
N-methyl-N'-t-butyl-N-(1-naphthoyl)-N'-benzoylhydrazine
N-methyl-N'-t-butyl-N,N'-dinaphthoyl hydrazine
N-methyl-N'-t-butyl-N-(3-chlorobenzoyl)-N'-benzoylhydrazine
N-methyl-N'-t-butyl-N-(4-chlorobenzoyl)-N'-(3,4-dichlorobenzoyl)hydrazine
N-methyl-N'-t-butyl-N-(2-chlorobenzoyl)-N'-(3,4-dichlorobenzoyl)hydrazine
N-methyl-N'-t-butyl-N-(2-toluoyl)-N'-benzoylhydrazine
N-methyl-N'-t-butyl-N-benzoyl-N'-(2-chloro-4-nitrobenzoyl)hydrazine
N-methyl-N'-t-butyl-N-benzoyl-N'-(3,5-dinitrobenzoyl)hydrazine
N-methyl-N'-t-butyl-N-benzoyl-N'-(2,3-dichlorobenzoyl)hydrazine
N-methyl-N'-(1,2,2-trimethylethyl)-N,N'-dibenzoylhydrazine
N-methyl-N'-t-butyl-N-benzoyl-N'-(2-chloro-5-methylbenzoyl)hydrazine
N-methyl-N'-t-butyl-N-benzoyl-N'-(3,5-dimethylbenzoyl)hydrazine N-methyl-N'-t-butyl-N-benzoyl-N'-(2-nitro-5-methylbenzoyl)hydrazine
N-methyl-N'-t-butyl-N-benzoyl-N'-(2-methyl-3-chlorobenzoyl)hydrazine
N-methyl-N'-t-butyl-N-benzoyl-N'-(3-chloro-4-methylbenzoyl)hydrazine
N-methyl-N'-t-butyl-N-benzoyl-N'-(2-nitro-3-chlorobenzoyl)hydrazine
N-methyl-N'-t-butyl-N-benzoyl-N'-(3-methoxy-4-nitrobenzoyl)hydrazine
N-methyl-N'-t-butyl-N-benzoyl-N'-(2-nitro-3-methoxybenzoyl)hydrazine
N-methyl-N'-t-butyl-N-benzoyl-N'-(2,4-dinitrobenzoyl)hydrazine
N-methyl-N'-t-butyl-N-(4-chlorobenzoyl)-N'-(2-chlorobenzoyl)hydrazine
N-methyl-N'-t-butyl-N-(4-chlorobenzoyl)-N'-(3-chlorobenzoyl)hydrazine
N-methyl-N'-t-butyl-N-(4-chlorobenzoyl)-N'-(4-toluoyl)hydrazine
N-methyl-N'-t-butyl-N-(4-chlorobenzoyl)-N'-(3,5-dichlorobenzoyl)hydrazine
N-methyl-N'-t-butyl-N-(4-chlorobenzoyl)-N'-(2,4-dichlorobenzoyl)hydrazine
N-methyl-N'-t-butyl-N-(4-chlorobenzoyl)-N'-(4-trifluoromethylbenzoyl)hydrazine
N-methyl-N'-t-butyl-N-benzoyl-N'-(4-methanesulfonyloxybenzoyl)hydrazine
N-methyl-N'-t-butyl-N-benzoyl-N'-(4-isopropylbenzoyl)hydrazine
N-methyl-N'-t-butyl-N-benzoyl-N'-(2-acetoxybenzoyl)hydrazine
N-methyl-N'-t-butyl-N-benzoyl-N'-(4-ethylbenzoyl)hydrazine
N-methyl-N'-t-butyl-N-benzoyl-N'-(2-bromobenzoyl)hydrazine
N-methyl-N'-t-butyl-N-benzoyl-N'-(4-hydroxybenzoyl)hydrazine
N-methyl-N'-t-butyl-N-(4-toluoyl)-N'-(2-toluoyl)hydrazine
N-methyl-N'-t-butyl-N-(4-toluoyl)-N'-(3-toluoyl)hydrazine
N-methyl-N'-t-butyl-N-(4-toluoyl)-N'-(2,4-dichlorobenzoyl)hydrazine
N-methyl-N'-t-butyl-N-(4-toluoyl)-N'-(3,5-dichlorobenzoyl)hydrazine
N-methyl-N'-t-butyl-N-(4-toluoyl)-N'-(2-chlorobenzoyl)hydrazine
N-methyl-N'-t-butyl-N-(4-toluoyl)-N'-(4-fluorobenzoyl)hydrazine
N-methyl-N'-t-butyl-N-(4-toluoyl)-N'-(4-trifluoromethylbenzoyl)hydrazine
N-methyl-N'-t-butyl-N-(4-toluoyl)-N'-(3-chlorobenzoyl)hydrazine
N-methyl-N'-t-butyl-N-(4-chlorobenzoyl)-N'-(3-chlorobenzoyl)hydrazine
N-methyl-N'-t-butyl-N-(4-chlorobenzoyl)-N'-(4-chloromethylbenzoyl)hydrazine
N-methyl-N'-t-butyl-N-(4-chlorobenzoyl)-N'-(2-toluoyl)hydrazine
N-methyl-N'-t-butyl-N-(4-chlorobenzoyl)-N'-(3-anisoyl)hydrazine
N-methyl-N'-t-butyl-N-(4-chlorobenzoyl)-N'-(3-toluoyl)hydrazine
N-methyl-N'-t-butyl-N,N'-bis(4-fluorobenzoyl)hydrazine
N-methyl-N'-t-butyl-N,N'-bis(3-fluorobenzoyl)hydrazine
N-methyl-N'-t-butyl-N,N'-bis(2-fluorobenzoyl)hydrazine
N-methyl-N'-t-butyl-N,N'-bis(2-naphthoyl)hydrazine
N-methyl-N'-t-butyl-N-(4-isobutylbenzoyl)-N'-(2-nitrobenzoyl)hydrazine
N-methyl-N'-t-butyl-N-(2-bromobenzoyl)-N'-(4-ethenylbenzoyl)hydrazine
N-methyl-N'-t-butyl-N-(4-toluoyl)-N'-(4-ethynylbenzoyl)hydrazine
N-methyl-N'-t-butyl-N-[4-(1-hydroxy-2-propynyl)benzoyl]-N'-(3,4-methylenedioxybenzoyl)hydrazine
N-methyl-N'-t-butyl-N-(3-phenoxybenzoyl)-N'-(2-bromobenzoyl)hydrazine
N-methyl-N'-t-butyl-N-(2,4-dichlorobenzoyl)-N'-(4-trifluoromethoxybenzoyl)hydrazine
N-methyl-N'-t-butyl-N-(4-ethylbenzoyl)-N'-(2-difluoromethoxy-4-chlorobenzoyl)hydrazine
N-methyl-N'-isopropyl-N'-(4-chloro-2-bromobenzoyl)-N-benzoylhydrazine
N-methyl-N'-(2,2-dimethylethyl)-N-(3-bromomethylbenzoyl)-N'-(4-isopropyloxybenzoyl)hydrazine
N-methyl-N'-t-butyl-N-(4-chloromethylbenzoyl)-N'-(2-carboxybenzoyl)hydrazine
N-methyl-N'-(1-methylpropyl)-N-(4-carboxybenzoyl)-N'-(3,4,5-trichlorobenzoyl)hydrazine
N-methyl-N'-t-butyl-N-(4-propanoylbenzoyl)-N'-[4-(4-pentenyl)benzoyl]hydrazine
N-methyl-N'-(1,2,2-trimethylpropyl)-N-[2-(ethoxy-1-ethoxyl)benzoyl]-N'-[4-(2-ethylbutanoyl)benzoyl]hydrazine
N-methyl-N'-t-butyl-N-(6-bromo-2-naphthoyl)-N'-(4-benzoylbenzoyl)hydrazine
N-methyl-N'-isopropyl-N-(4-(2-pentynoyl)benzoyl)-N'-(3-nitrobenzoyl)hydrazine
N-methyl-N'-t-butyl-N-(4-bromo-2-cyanobenzoyl)-N'-(6-(5-oxotetrahydronaphthoyl)hydrazine
N-methyl-N'-(2,2-dimethylpropyl)-N-(4-t-butyloxycarbonyl-benzoyl)-N'-(4-chloro-3-trifluoromethoxybenzoyl)hydrazine
N-methyl-N'-t-butyl-N-(2-benzyloxycarbonylbenzoyl)-N'-(2-methoxy-4-bromobenzoyl)hydrazine
N-methyl-N'-t-butyl-N-(4-(2,2,2-trifluoroethoxycarbonyl)-3-methylbenzoyl-N'-(2,4-dichloro-3-hydroxybenzoyl)-hydrazine
N-methyl-N'-isopropyl-N-(3-propanoyloxybenzoyl)-N'-(2,5-dibromobenzoyl)hydrazine
N-methyl-N'-(1,2,2-trimethylpropyl)-N-(4-propylbenzoyl)-N'-(3-ethoxycarbonyloxybenzoyl)hydrazine
N-methyl-N'-t-butyl-N-(3,5-dimethylbenzoyl)-N'-(4-t-butylcarbonyloxybenzoyl)hydrazine
N-methyl-N'-(1-methylpropyl)-N-(2-aminobenzoyl)-N'-(3,4-dichlorobenzoyl)hydrazine
N-methyl-N'-t-butyl-N-(4-chloro-2-trifluoromethoxybenzoyl)-N'-(4-methylaminobenzoyl)hydrazine
N-methyl-N'-t-butyl-N-(4-dimethylaminobenzoyl)-N'-(4-acetylaminobenzoyl)hydrazine
N-methyl-N'-t-butyl-N-(3-formylbenzoyl)-N'-(2-chloro-4-(N-hydroxyformiminoyl)benzoyl)hydrazine
N-methyl-N'-t-butyl-N-(2-methanesulfonylaminobenzoyl)-N'-(2-chloro-3-(N'-phenylhydrazinoformyl)-benzoyl)hydrazine
N-methyl-N'-(1-methylpropyl)-N-(2-aminocarbonylbenzoyl)-N'-(2-chloro-4-ethylaminocarbonylbenzoyl)hydrazine
N-methyl-N'-isopropyl-N-(4-methyl-3-dimethylaminocarbonylbenzoyl)-N'-(4-trifluoromethylbenzoyl)hydrazine N-methyl-N'-(1,2,2-trimethylpropyl)-N-(4-trifluoromethoxy-2-chlorobenzoyl)-N'-(4-methoxycarbonylaminobenzoyl)hydrazine
N-methyl-N'-t-butyl-N-(2-carboxymethylbenzoyl)-N'-(4-dimethylaminocarbonyloxybenzoyl)hydrazine
N-methyl-N'-t-butyl-N-(3-methylaminocarbonyloxybenzoyl)-N'-(2-chloro-4-(N-acetoxyaminocarbonyloxy)benzoylhydrazine
N-methyl-N'-isopropyl-N-(4-methoxy-3-bromobenzoyl)-N'-(4-sulfhydrylbenzoyl)hydrazine
N-methyl-N'-(1-methylpropyl)-N-(3-chloro-5-sulfhydryl-benzoyl)-N'-(3-phenylazobenzoyl)hydrazine
N-methyl-N'-(2,2-dimethylpropyl)-N-(2-methylthiobenzoyl)-N'-(2-chloro-4-(1,3-dioxolano-2-ylbenzoyl)hydrazine
N-methyl-N'-t-butyl-N-(3-methanesulfinylbenzoyl)-N'-(3,4,5-trimethoxybenzoyl)hydrazine
N-methyl-N'-(1,2,2-trimethylpropyl)-N-(3-phenylsulfonylbenzoyl)-N'-(3,4-dichlorobenzoyl)hydrazine
N-methyl-N'-t-butyl-N-(3-trifluoromethanesulfonyloxybenzoyl)-N'-(2-chloro-4-trichloromethylthiobenzoyl)hydrazine
N-methyl-N'-t-butyl-N-(2-iodobenzoyl)-N'-(4-aminosulfonyloxy)hydrazine
N-methyl-N'-t-butyl-N-(2,5-dichlorobenzoyl)-N'-(4-trimethylsilylbenzoyl)hydrazine
N-methyl-N'-(1,2,2-trimethylpropyl)-N-(4-acetylthiobenzoyl)-N'-(3,4-dichlorobenzoylhydrazine
N-methyl-N'-t-butyl-N-(methylthiocarbonylthioxybenzoyl)-N'-(3-chloro-4-formylaminobenzoyl)hydrazine
N-methyl-N'-t-butyl-N-(3-methylthiocarbonylbenzoyl)-N'-(4-pentafluoroethoxybenzoyl)hydrazine
N-methyl-N'-(t-butyl)-N-(pentafluorobenzoyl)-N'-(4-phenylaminobenzoyl)hydrazine
N-methyl-N'-(t-butyl)-N-(6-chlorophenylbenzoyl)-N'-(3-chloro-4-acetylaminobenzoyl)hydrazine
N-methyl-N'-isopropyl-N-(3-hydroxyaminobenzoyl)-N'-(4-tribromomethylbenzoyl)hydrazine
N-methyl-N'-(1,2,2-trimethylpropyl)-N-(4-aminocarbonylaminobenzoyl)-N'-(2-bromobenzoyl)hydrazine
N-methyl-N'-(1-methylpropyl)-N-(4-fluoro-3-bromochloromethylbenzoyl)-N'-(3-cyanomethylbenzoyl)hydrazine
N-methyl-N'-t-butyl-N-(4-propylthiobenzoyl)-N'-(3,4-dichlorobenzoyl)hydrazine
N-methyl-N'-t-butyl-N-(4-chloromethylcarbonylbenzoyl)-N'-(2-bromobenzoyl)hydrazine
N-methyl-N'-t-butyl-N-(3-trichloroethenylbenzoyl)-N'-(4-fluorobenzoyl)hydrazine
N-methyl-N'-isopropyl-N-(4-(1,3-dimethylbutyl)benzoyl)-N'-(2-nitrobenzoyl)hydrazine
N-methyl-N'-t-butyl-N-(4-nitrosobenzoyl)-N'-(2,4-dichlorobenzoyl)hydrazine
N-methyl-N'-t-butyl-N-(4-(N'-methylformamidinoylbenzoyl)-N'-(3-chloro-4-bromobenzoyl)hydrazine
N-methyl-N'-isopropyl-N-(2,6-dichlorobenzoyl)-N'-(4-trifluoromethoxybenzoyl)hydrazine
N-methyl-N'-t-butyl-(2,3,4-trichlorobenzoyl)-N'-(2-nitrobenzoylhydrazine
N-methyl-N'-t-butyl-N-(2-chlorobenzoyl)-N'-(4-chlorosulfenylbenzoyl)hydrazine
N-methyl-N'-t-butyl-N-(4-allenylbenzoyl)-N'-(4-chlorobenzoyl)hydrazine
N-ethyl-N'-t-butyl-N,N'-bis(4-chlorobenzoyl)hydrazine
N-ethyl-N'-t-butyl-N,N'-bis(3-chlorobenzoyl)hydrazine
N-ethyl-N'-t-butyl-N,N'-dibenzoylhydrazine
N-ethyl-N'-t-butyl-N,N'-bis(3,4-dichlorobenzoyl)hydrazine
N-ethyl-N'-t-butyl-N,N'-bis(4-toluoyl)hydrazine
N-ethyl-N'-t-butyl-N,N'-bis(4-nitrobenzoyl)hydrazine
N-ethyl-N'-t-butyl-N,N'-bis(4-anisoyl)hydrazine
N-ethyl-N'-t-butyl-N,N'-bis(3-nitrobenzoyl)hydrazine
N-ethyl-N'-t-butyl-N,N'-bis(3-anisoyl)hydrazine
N-ethyl-N'-t-butyl-N,N'-bis(2-nitrobenzoyl)hydrazine
N-ethyl-N'-t-butyl-N,N'-bis(2-chlorobenzoyl)hydrazine
N-ethyl-N'-t-butyl-N,N'-bis(2-anisoyl)hydrazine
N-ethyl-N'-t-butyl-N-(4-toluoyl)-N'-benzoylhydrazine
N-ethyl-N'-t-butyl-N,N'-bis(4-cyanobenzoyl)hydrazine
N-ethyl-N'-t-butyl-N-(4-toluoyl)-N'-(4-chlorobenzoyl)hydrazine
N-ethyl-N'-t-butyl-N-benzoyl-N'-(4-chlorobenzoyl)hydrazine
N-ethyl-N'-t-butyl-N-benzoyl-N'-(3-chlorobenzoyl)hydrazine
N-ethyl-N'-t-butyl-N-benzoyl-N'-(2-chlorobenzoyl)hydrazine
N-ethyl-N'-t-butyl-N,N'-bis(3-toluoyl)hydrazine
N-ethyl-N'-t-butyl-N,N'-bis(2-toluoyl)hydrazine
N-ethyl-N'-t-butyl-N-benzoyl-N'-(4-toluoyl)hydrazine
N-ethyl-N'-t-butyl-N-benzoyl-N'-(3-toluoyl)hydrazine
N-ethyl-N'-t-butyl-N-benzoyl-N'-(2-toluoyl)hydrazine
N-ethyl-N'-t-butyl-N-benzoyl-N'-(4-anisoyl)hydrazine
N-ethyl-N'-t-butyl-N-benzoyl-N'-(3-anisoyl)hydrazine
N-ethyl-N'-t-butyl-N-benzoyl-N'-(2-anisoyl)hydrazine
N-ethyl-N'-t-butyl-N-benzoyl-N'-(4-n-butylbenzoyl)hydrazine
N-ethyl-N'-t-butyl-N-benzoyl-N'-(4-cyanobenzoyl)hydrazine
N-ethyl-N'-t-butyl-N-benzoyl-N'-(4-nitrobenzoyl)hydrazine
N-ethyl-N'-t-butyl-N-benzoyl-N'-(3-nitrobenzoyl)hydrazine
N-ethyl-N'-t-butyl-N-benzoyl-N'-(2-nitrobenzoyl)hydrazine
N-ethyl-N'-t-butyl-N,N'-bis(4-t-butylbenzoyl)hydrazine
N-ethyl-N'-t-butyl-N-(4-toluoyl)-N'-(3,4-dichlorobenzoyl)hydrazine
N-ethyl-N'-t-butyl-N-benzoyl-N'-(4-fluorobenzoyl)hydrazine
N-ethyl-N'-t-butyl-N-benzoyl-N'-(3-fluorobenzoyl)hydrazine
N-ethyl-N'-t-butyl-N-benzoyl-N'-(2-fluorobenzoyl)hydrazine
N-ethyl-N'-t-butyl-N-benzoyl-N'-(2,4-dichlorobenzoyl)hydrazine
N-ethyl-N'-isopropyl-N,N'-dibenzoylhydrazine
N-ethyl-N'-t-butyl-N-benzoyl-N'-(4-trifluoromethylbenzoyl)hydrazine
N-ethyl-N'-t-butyl-N-benzoyl-N'-(3-trifluoromethylbenzoyl)hydrazine
N-ethyl-N'-t-butyl-N-benzoyl-N'-(2-trifluoromethylbenzoyl)hydrazine
N-ethyl-N'-t-butyl-N-benzoyl-N'-(2,5-difluorobenzoyl)hydrazine
N-ethyl-N'-(2,2-dimethylethyl)-N,N'-dibenzoylhydrazine
N-ethyl-N'-t-butyl-N-benzoyl-N'-(3-cyanobenzoyl)hydrazine
N-ethyl-N'-(1-methylpropyl)-N,N'-dibenzoylhydrazine
N-ethyl-N'-t-butyl-N-benzoyl-N'-(2,6-difluorobenzoyl)hydrazine
N-ethyl-N'-t-butyl-N-(4-chlorobenzoyl)-N'-benzoylhydrazine
N-ethyl-N'-t-butyl-N-benzoyl-N'-(3,4-dichlorobenzoyl)hydrazine N-ethyl-N'-t-butyl-N-benzoyl-N'-(3,5-dichlorobenzoyl)hydrazine
N-ethyl-N'-t-butyl-N-benzoyl-N'-(2,6-dichlorobenzoyl)hydrazine
N-ethyl-N'-t-butyl-N-(4-t-butylbenzoyl)-N40 -benzoylhydrazine
N-ethyl-N'-t-butyl-N-(2-chlorobenzoyl)-N'-benzoylhydrazine
N-ethyl-N'-t-butyl-N-(1-naphthoyl)-N'-benzoylhydrazine
N-ethyl-N'-t-butyl-N,N'-dinaphthoylhydrazine
N-ethyl-N'-t-butyl-N-(3-chlorobenzoyl)-N'-benzoylhydrazine
N-ethyl-N'-t-butyl-N-(4-chlorobenzoyl)-N'-(3,4-dichlorobenzoyl)hydrazine
N-ethyl-N'-t-butyl-N-(2-chlorobenzoyl)-N'-(3,4-dichlorobenzoyl)hydrazine
N-ethyl-N'-t-butyl-N-(2-toluoyl)-N'-benzoylhydrazine
N-ethyl-N'-t-butyl-N-benzoyl-N'-(2-chloro-4-nitrobenzoyl)hydrazine
N-ethyl-N'-t-butyl-N-benzoyl-N'-(3,5-dinitrobenzoyl)hydrazine
N-ethyl-N'-t-butyl-N-benzoyl-N'-(2,3-dichlorobenzoyl)hydrazine
N-ethyl-N'-(1,2,2-trimethylethyl)-N,N'-dibenzoylhydrazine
N-ethyl-N'-t-butyl-N-benzoyl-N'-(2-chloro-5-methylbenzoyl)hydrazine
N-ethyl-N'-t-butyl-N-benzoyl-N'-(3,5-dimethylbenzoyl)hydrazine
N-ethyl-N'-t-butyl-N-benzoyl-N'-(2-nitro-5-methylbenzoyl)hydrazine
N-ethyl-N'-t-butyl-N-benzoyl-N'-(2-methyl-3-chlorobenzoyl)hydrazine
N-ethyl-N'-t-butyl-N-benzoyl-N'-(3-chloro-4-methylbenzoyl)hydrazine
N-ethyl-N'-t-butyl-N-benzoyl-N'-(2-nitro-3-chlorobenzoyl)hydrazine
N-ethyl-N'-t-butyl-N-benzoyl-N'-(3-methoxy-4-nitrobenzoyl)hydrazine
N-ethyl-N'-t-butyl-N-benzoyl-N'-(2-nitro-3-methoxybenzoyl)hydrazine
N-ethyl-N'-t-butyl-N-benzoyl-N'-(2,4-dinitrobenzoyl)hydrazine
N-ethyl-N'-t-butyl-N-(4-chlorobenzoyl)-N'-(2-chlorobenzoyl)hydrazine
N-ethyl-N'-t-butyl-N-(4-chlorobenzoyl)-N'-(3-chlorobenzoyl)hydrazine
N-ethyl-N'-t-butyl-N-(4-chlorobenzoyl)-N'-(4-toluoyl)hydrazine
N-ethyl-N'-t-butyl-N-(4-chlorobenzoyl)-N'-(3,5-dichlorobenzoyl)hydrazine
N-ethyl-N'-t-butyl-N-(4-chlorobenzoyl)-N'-(2,4-dichlorobenzoyl)hydrazine
N-ethyl-N'-t-butyl-N-(4-chlorobenzoyl)-N'-(4-trifluoromethylbenzoyl)hydrazine
N-ethyl-N'-t-butyl-N-benzoyl-N'-(4-methanesulfonyloxybenzoyl)hydrazine
N-ethyl-N'-t-butyl-N-benzoyl-N'-(4-isopropylbenzoyl)hydrazine
N-ethyl-N'-t-butyl-N-benzoyl-N'-(2-acetoxybenzoyl)hydrazine
N-ethyl-N'-t-butyl-N-benzoyl-N'-(4-ethylbenzoyl)hydrazine
N-ethyl-N'-t-butyl-N-benzoyl-N'-(2-bromobenzoyl)hydrazine
N-ethyl-N'-t-butyl-N-benzoyl-N'-(4-hydroxybenzoyl)hydrazine
N-ethyl-N'-t-butyl-N-(4-toluoyl)-N'-(2-toluoyl)hydrazine
N-ethyl-N'-t-butyl-N-(4-toluoyl)-N'-(3-toluoyl)hydrazine
N-ethyl-N'-t-butyl-N-(4-toluoyl)-N'-(2,4-dichlorobenzoyl)hydrazine
N-ethyl-N'-t-butyl-N-(4-toluoyl)-N'-(3,5-dichlorobenzoyl)hydrazine
N-ethyl-N'-t-butyl-N-(4-toluoyl)-N'-(2-chlorobenzoyl)hydrazine
N-ethyl-N'-t-butyl-N-(4-toluoyl)-N'-(4-fluorobenzoyl)hydrazine
N-ethyl-N'-t-butyl-N-(4-toluoyl)-N'-(4-trifluoromethylbenzoyl)hydrazine
N-ethyl-N'-t-butyl-N-(4-toluoyl)-N'-(3-chlorobenzoyl)hydrazine
N-ethyl-N'-t-butyl-N-(4-chlorobenzoyl)-N'-(3-chlorobenzoyl)hydrazine
N-ethyl-N'-t-butyl-N-(4-chlorobenzoyl)-N'-(4-chloromethylbenzoyl)hydrazine
N-ethyl-N'-t-butyl-N-(4-chlorobenzoyl)-N'-(2-toluoyl)hydrazine
N-ethyl-N'-t-butyl-N-(4-chlorobenzoyl)-N'-(3-anisoyl)hydrazine
N-ethyl-N'-t-butyl-N-(4-chlorobenzoyl)-N'-(3-toluoyl)hydrazine
N-ethyl-N'-t-butyl-N,N'-bis(4-fluorobenzoyl)hydrazine
N-ethyl-N'-t-butyl-N,N'-bis(3-fluorobenzoyl)hydrazine
N-ethyl-N'-t-butyl-N,N'-bis(2-fluorobenzoyl)hydrazine
N-ethyl-N'-t-butyl-N,N'-bis(2-naphthoyl)hydrazine
N-ethyl-N'-t-butyl-N-(4-isobutylbenzoyl)-N'-(2-nitrobenzoyl)hydrazine
N-ethyl-N'-t-butyl-N-(2-bromobenzoyl)-N'-(4-ethenylbenzoyl)hydrazine
N-ethyl-N'-t-butyl-N-(4-toluoyl)-N'-(4-ethynylbenzoyl)hydrazine
N-ethyl-N'-t-butyl-N-[4-(1-hydroxy-2-propynyl)benzoyl]-N'-(3,4-methylenedioxybenzoyl)hydrazine
N-ethyl-N'-t-butyl-N-(3-phenoxybenzoyl)-N'-(2-bromobenzoyl)hydrazine
N-ethyl-N'-t-butyl-N-(2,4-dichlorobenzoyl)-N'-(4-trifluoromethoxybenzoyl)hydrazine
N-ethyl-N'-t-butyl-N-(4-ethylbenzoyl)-N'-(2-difluoromethoxy-4-chlorobenzoyl)hydrazine
N-ethyl-N'-isopropyl-N'-(4-chloro-2-bromobenzoyl)-N-benzoylhydrazine
N-ethyl-N'-(2,2-dimethylethyl)-N-(3-bromomethylbenzoyl)-N'-(4-isopropyloxybenzoyl)hydrazine
N-ethyl-N'-t-butyl-N-(4-chloromethylbenzoyl)-N'-(2-carboxybenzoyl)hydrazine
N-ethyl-N'-(1-methylpropyl)-N-(4-carboxybenzoyl)-N'-(3,4,5-trichlorobenzoyl)hydrazine
N-ethyl-N'-t-butyl-N-(4-propanoylbenzoyl)-N'-[4-(4-pentenyl)benzoyl]hydrazine
N-ethyl-N'-(1,2,2-trimethylpropyl)-N-[2-(ethoxy-1-ethoxyl)benzoyl]-N'-[4-(2-ethylbutanoyl)benzoyl]hydrazine
N-ethyl-N'-t-butyl-N-(6-bromo-2-naphthoyl)-N'-(4-benzoylbenzoyl)hydrazine
N-ethyl-N'-isopropyl-N-(4-(2-pentynoyl)benzoyl)-N'-(3-nitrobenzoyl)hydrazine
N-ethyl-N'-t-butyl-N-(4-bromo-2-cyanobenzoyl)-N'-(6-(5-oxotetrahydronaphthoyl)hydrazine
N-ethyl-N'-(2,2-dimethylpropyl)-N-(4-t-butyloxycarbonylbenzoyl)-N'-(4-chloro-3-trifluoromethoxybenzoyl)hydrazine
N-ethyl-N'-t-butyl-N-(2-benzyloxycarbonylbenzoyl)-N'-(2-methoxy-4-bromobenzoyl)hydrazine N-ethyl-N'-t-butyl-N-(4-(2,2,2-trifluoroethoxycarbonyl)-3-methylbenzoyl)-N'-(2,4-dichloro-3-hydroxybenzoyl)hydrazine
N-ethyl-N'-isopropyl-N-(3-propanoyloxybenzoyl)-N'-(2,5-dibromobenzoyl)hydrazine
N-ethyl-N'-(1,2,2-trimethylpropyl)-N-(4-propylbenzoyl)-N'-(3-ethoxycarbonyloxybenzoyl)hydrazine
N-ethyl-N'-t-butyl-N-(3,5-dimethylbenzoyl)-N'-(4-t-butylcarbonyloxybenzoyl)hydrazine
N-ethyl-N'-(1-methylpropyl)-N-(2-aminobenzoyl)-N'-(3,4-dichlorobenzoyl)hydrazine
N-ethyl-N'-t-butyl-N-(4-chloro-2-trifluoromethoxybenzoyl)-N'-(4-methylaminobenzoyl)hydrazine
N-ethyl-N'-t-butyl-N-(4-dimethylaminobenzoyl)-N'-(4-acetylaminobenzoyl)hydrazine
N-ethyl-N'-t-butyl-N-(3-formylbenzoyl)-N'-(2-chloro-4-(N-hydroxyformiminoyl)benzoyl)hydrazine
N-ethyl-N'-t-butyl-N-(2-methanesulfonylaminobenzoyl)-N'-(2-chloro-3-(N'-phenylhydrazinoformyl)benzoyl)hydrazine
N-ethyl-N'-(1-methylpropyl)-N-(2-aminocarbonylbenzoyl)-N'-(2-chloro-4-ethylaminocarbonylbenzoyl)hydrazine
N-ethyl-N'-isopropyl-N-(4-methyl-3-dimethylaminocarbonylbenzoyl)-N'-(4-trifluoromethylbenzoyl)hydrazine
N-ethyl-N'-(1,2,2-trimethylpropyl)-N-(4-trifluoromethoxy-2-chlorobenzoyl)-N'-(4-methoxycarbonylaminobenzoyl)hydrazine
N-ethyl-N'-t-butyl-N-(2-carboxymethylbenzoyl)-N'-(4-dimethylaminocarbonyloxybenzoyl)hydrazine
N-ethyl-N'-t-butyl-N-(3-methylaminocarbonyloxybenzoyl)-N'-(2-chloro-4-(N-acetoxyaminocarbonyloxy)-benzoylhydrazine
N-ethyl-N'-isopropyl-N-(4-methoxy-3-bromobenzoyl)-N'-(4-sulfhydrylbenzoyl)hydrazine
N-ethyl-N'-(1-methylpropyl)-N-(3-chloro-5-sulfhydrylbenzoyl)-N'-(3-phenylazobenzoyl)hydrazine
N-ethyl-N'-(2,2-dimethylpropyl)-N-(2-methylthiobenzoyl)-N'-(2-chloro-4-(1,3-dioxolano-2-yl)benzoyl)hydrazine
N-ethyl-N'-t-butyl-N-(3-methanesulfinylbenzoyl)-N'-(3,4,5-trimethoxybenzoyl)hydrazine
N-ethyl-N'-(1,2,2-trimethylpropyl)-N-(3-phenylsulfonylbenzoyl)-N'-(3,4-dichlorobenzoyl)hydrazine
N-ethyl-N'-t-butyl-N-(3-trifluoromethanesulfonyloxybenzoyl)-N'-(2-chloro-4-trichloromethylthiobenzoyl)hydrazine
N-ethyl-N'-t-butyl-N-(2-iodobenzoyl)-N'-(4-aminosulfonyloxy)hydrazine
N-ethyl-N'-t-butyl-N-(2,5-dichlorobenzoyl)-N'-(4-trimethylsilylbenzoyl)hydrazine
N-ethyl-N'-(1,2,2-trimethylpropyl)-N-(4-acetylthiobenzoyl)-N'-(3,4-dichlorobenzoyl)hydrazine
N-ethyl-N'-t-butyl-N-(methylthiocarbonylthioxybenzoyl)-N'-(3-chloro-4-formylaminobenzoyl)hydrazine
N-ethyl-N'-t-butyl-N-(3-methylthiocarbonylbenzoyl)-N'-(4-pentafluoroethoxybenzoyl)hydrazine
N-ethyl-N'-(t-butyl)-N-(pentafluorobenzoyl)-N'-(4-phenylaminobenzoyl)hydrazine
N-ethyl-N'-(t-butyl)-N-(6-chlorophenylbenzoyl)-N'-(3-chloro-4-acetylaminobenzoyl)hydrazine
N-ethyl-N'-isopropyl-N-(3-hydroxyaminobenzoyl)-N'-(4-tribromomethylbenzoyl)hydrazine
N-ethyl-N'-(1,2,2-trimethylpropyl)-N-(4-aminocarbonylaminobenzoyl)-N'-(2-bromobenzoyl)hydrazine
N-ethyl-N'-(1-methylpropyl)-N-(4-fluoro-3-bromochloromethylbenzoyl)-N'-(3-cyanomethylbenzoyl)hydrazine
N-ethyl-N'-t-butyl-N-(4-propylthiobenzoyl)-N'-(3,4-dichlorobenzoyl)hydrazine
N-ethyl-N'-t-butyl-N-(4-chloromethylcarbonylbenzoyl)-N'-(2-bromobenzoyl)hydrazine
N-ethyl-N'-t-butyl-N-(3-trichloroethenylbenzoyl)-N'-(4-fluorobenzoyl)hydrazine
N-ethyl-N'-isopropyl-N-(4-(1,3-dimethylbutyl)benzoyl)-N'-(2-nitrobenzoyl)hydrazine
N-ethyl-N'-t-butyl-N-(4-nitrosobenzoyl)-N'-(2,4-dichlorobenzoyl)hydrazine
N-ethyl-N'-t-butyl-N-(4-(N'-methylformamidinoylbenzoyl)-N'-(3-chloro-4-bromobenzoyl)hydrazine
N-ethyl-N'-isopropyl-N-(2,6-dichlorobenzoyl)-N'-(4-trifluoromethoxybenzoyl)hydrazine
N-ethyl-N'-t-butyl-(2,3,4-trichlorobenzoyl)-N'-(2-nitrobenzoyl)hydrazine
N-ethyl-N'-t-butyl-N-(2-chlorobenzoyl)-N'-(4-chlorosulfenylbenzoyl)hydrazine
N-ethyl-N'-t-butyl-N-(4-allenylbenzoyl)-N'-(4-chlorobenzoyl)hydrazine
N-benzyl-N'-t-butyl-N-(4-chlorobenzoyl)-N'-(4-ethylbenzoyl)hydrazine
N-allyl-N'-t-butyl-N-(4-ethylbenzoyl)-N'-(3-ethylbenzoyl)hydrazine
N-benzyl-N'-t-butyl-N,N'-dibenzoylhydrazine
N-allyl-N'-t-butyl-N,N'-dibenzoylhydrazine
N-methoxymethyl-N'-t-butyl-N,N'-dibenzoylhydrazine
N-methylthiomethyl-N'-t-butyl-N,N'-dibenzoylhydrazine
N-methylthiomethyl-N'-t-butyl-N,N'-bis(4-chlorobenzoyl)hydrazine
N-methoxymethyl-N'-t-butyl-N-(2-chlorobenzoyl)-N'-(2,4-dichlorobenzoyl)hydrazine
N-phenylthiomethyl-N'-t-butyl-N-(4-toluoyl)-N'-(2-nitrobenzoyl)hydrazine
N-trimethylsiloxymethyl-N'-2,2-dimethylpropyl-N-(4-methoxy-3-chlorobenzoyl)-N'-benzoylhydrazine
N-isopropyl-N'-2,2-dimethylpropyl-N-(4-chlorobenzoyl)-N'-(3-ethylbenzoyl)hydrazine
N-propargyl-N'-(2,2-dimethylpropyl)-N-(4-toluoyl)-N'-(2-bromobenzoyl)hydrazine
N-propyl-N'-t-butyl-N-(3-ethoxybenzoyl)-N'-(2-bromobenzoyl)hydrazine
N-hexyl-N'-t-butyl-N-(3,4-dichlorobenzoyl)-N'-(2-nitrobenzoyl)hydrazine
N-(3,5-dinitrobenzyl)-N'-t-butyl-N,N'-bis(2-chlorobenzoyl)hydrazine
N-(2,4-dichlorobenzyl)-N'-(1,2,2-trimethylpropyl)-N-(4-bromobenzoyl)-N'-(3-toluoyl)hydrazine
N-(4-methoxybenzyl)-N'-(2,2-trimethylpropyl)-N-(4-ethoxybenzoyl)-N'-(3-chlorobenzoyl)hydrazine
N-(3-nitrobenzyl)-N'-isopropyl-N-(4-ethylbenzoyl)-N'-(3-toluoyl)hydrazine
N-allyl-N'-isopropyl-N-(4-toluoyl)-N'-(4-chlorobenzoyl)hydrazine
N-allyl-N'-(1,2,2-trimethylpropyl)-N-(3-methoxybenzoyl)N'-benzoylhydrazine
N-propyl-N'-isopropyl-N-(4-methylthiobenzoyl)-N'-(3,4-dichlorobenzoyl)hydrazine
N-propargyl-N'-t-butyl-N-(4-ethylbenzoyl)-N'-(3,5-dimethylbenzoyl)hydrazine
N-methoxymethyl-N'-t-butyl-N-(4-iodobenzoyl)-N'-(3,5-dichlorobenzoyl)hydrazine
N-methoxymethyl-N'-t-butyl-N-(4-propylbenzoyl)-N'-(4-chlorobenzoyl)hydrazine N-methoxymethyl-N'-t-butyl-N-(4-vinylbenzoyl)-N'-(3,5-dichlorobenzoyl)hydrazine N-methylthiomethyl-N'-t-butyl-N-(4-toluoyl)-N'-(2-nitrobenzoyl)hydrazine N-methylthiomethyl-N'-t-butyl-N-(2-chlorobenzoyl)-N'-(3-toluoyl)hydrazine N-methylthiomethyl-N'-isopropyl-N-(anisoyl)-N'-benzoylhydrazine N-phenylthiomethyl-t-butyl-N-(4-toluoyl)-N'-(3,4-dichlorobenzoyl)hydrazine N-(trimethylsilyloxymethyl)-N'-(4-ethylbenzoyl)-N'-(2-chloro-5-methylbenzoyl)hydrazine Because of their good insecticidal activity, compounds of the present invention for use in the insecticidal compositions and formulations include those where, independently X and X' are O or S;

$R^1$ is unsubstituted ($C_4$-$C_8$)alkyl including a tertiary carbon atom;

$R^2$ is ($C_1$-$C_4$)alkyl; ($C_1$-$C_4$)alkoxyalkyl having independently the stated number of carbon atoms in each alkyl group; methylthiomethyl; ($C_2$-$C_5$)alkenyl; ($C_2$-$C_5$)alkynyl; or benzyl where the phenyl ring is unsubstituted or substituted with halo, nitro, ($C_1$-$C_4$)alkyl or ($C_1$-$C_4$)alkoxy; and A and B are the same or different unsubstituted naphthyl; or unsubstituted phenyl or substituted phenyl where the substituents can be from one to three of the same or different halo; nitro; cyano; ($C_1$-$C_4$)alkyl; lower ($C_1$-$C_4$)haloalkyl; ($C_1$-$C_4$)cyanoalkyl; lower ($C_1$-$C_4$)alkoxy; ($C_1$-$C_4$)haloalkoxy; —COZ; carboxy; ($C_1$-$C_4$)alkoxycarbonyl; ($C_1$-$C_4$)alkanoyloxy; ($C_3$-$C_6$)alkenyl; ($C_3$-$C_6$)alkadienyl; ($C_2$-$C_6$)alkynyl; amino, ($C_1$-$C_4$)alkylamino or ($C_1$-$C_4$)dialkyamino having independently the stated number of carbon atoms in each alkyl group; thiocyanato; ($C_1$-$C_4$)alkylthio; —CSZ; $CS_2Z$; —SCOZ; ($C_1$-$C_4$)trialkylsilyl having independently the stated number of carbon atoms in each alkyl group; unsubstituted phenyl; substituted phenyl having one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or when two adjacent positions on the phenyl ring are substituted with alkoxy groups, these groups may be joined to form a 5- or 6-membered dioxolano or dioxano heterocyclic ring;

where Z and Z' are hydrogen or ($C_1$-$C_4$)alkyl; and agronomically acceptable salts.

Insecticidal compounds of the present invention having very good activity for use in the insecticidal compositions and formulations of the present invention include those where, independently, X and X' are O or S;

$R^1$ is ($C_4$-$C_7$)alkyl including a tertiary carbon atom;

$R^2$ is methyl; ethyl; ($C_1$-$C_2$)alkoxyalkyl having independently the stated number of carbon atoms in each alkyl group; ($C_2$-$C_5$)alkenyl; ($C_2$-$C_5$)alkynyl; or benzyl where the phenyl ring is unsubstituted or substituted with halo; and A and B are the same or different unsubstituted naphthyl; or unsubstituted phenyl or substituted phenyl having one to three of the same or different halo; nitro; cyano; lower ($C_1$-$C_4$)alkyl; ($C_1$-$C_4$)haloalkyl; lower ($C_1$-$C_4$)cyanoalkyl; ($C_1$-$C_4$)alkoxy; ($C_1$-$C_4$)alkoxyalkyl having independently the stated number of carbon atoms in each alkyl group; —COZ; ($C_1$-$C_4$)alkoxycarbonyl; ($C_1$-$C_4$)alkanoyloxy; thiocyanato; unsubstituted phenyl; substituted phenyl having one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or phenoxy where the phenyl ring is unsubstituted or substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group where Z is hydrogen or ($C_1$-$C_4$)alkyl; and agronomically acceptable salts thereof.

Because of their excellent insecticidal activity, preferred compounds of the present invention include those where, independently, X and X' are O;

$R^1$ is t-butyl; neopentyl (2,2-dimethylpropyl) or 1,2,2-trimethylpropyl;

$R^2$ is methyl; methoxymethyl; ($C_2$-$C_4$)alkenyl; ($C_2$-$C_5$)alkynyl; benzyl or 4-halobenzyl; and A and B are the same or different unsubstituted phenyl or substituted phenyl where the substituents are one to three of the same or different halo, nitro, lower ($C_1$-$C_4$)alkyl, ($C_1$-$C_4$)alkoxy, or ($C_1$-$C_4$)haloalkyl; and agronomically acceptable salts thereof.

Because of their outstanding insecticidal activity, particularly preferred compounds of the present invention include those where, independently, X and X' are O;

$R^1$ is t-butyl;

$R^2$ is ($C_2$-$C_5$)alkynyl; provided that the alpha and beta carbons are not secondary or tertiary carbon atoms; and A and B are unsubstituted phenyl or substituted phenyl where the substituents are one or two of the same or different chloro, fluoro, bromo, iodo, methyl, ethyl, methoxy or trifluoromethyl; and agronomically acceptable salts thereof.

Those N-substituted-N'-substituted-N,N'-diacyl hydrazines of Formula I which possess acidic or basic functional groups may be further reacted to form novel salts with appropriate bases or acids. These salts also exhibit insecticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. The ammonium salts include those in which the ammonium cation has the formula $NR^5R^6R^7R^8$ wherein each of $R^5$, $R^6$, $R^7$ and $R^8$ are independently hydrogen, hydroxy, ($C_1$-$C_4$)alkoxy, ($C_1$-$C_{20}$)alkyl, ($C_3$-$C_8$)alkenyl, ($C_3$-$C_8$)alkynyl, ($C_2$-$C_8$)hydroxyalkyl, ($C_2$-$C_8$)alkoxyalkyl, ($C_2$-$C_6$)aminoalkyl, ($C_2$-$C_6$)haloalkyl, amino, ($C_1$-$C_4$)alkyl- or ($C_1$-$C_4$)dialkylamino, substituted or unsubstituted phenyl, substituted or unsubstituted phenylalkyl, having up to four carbon atoms in the alkyl moiety, or any two of $R^5$, $R^6$, $R^7$ or $R^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^5$, $R^6$, $R^7$ or $R^8$ can be taken together to form with the nitrogen atom a 5- or 6-membered aromatic heterocyclic ring, such as piperazole or pyridine. When $R^5$, $R^6$, $R^7$ or $R^8$ substituent in the ammonium group is a substituted phenyl or substituted phenylalkyl, the substituents on the phenyl and phenylalkyl will generally be selected from halo, ($C_1$-$C_8$)alkyl, ($C_1$-$C_4$)alkoxy, hydroxy, nitro, trifluoromethyl, cyano, amino, ($C_1$-$C_4$)alkylthio and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxy-ethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate and the like.

The compounds of this invention or their precursors can be prepared by reacting a suitably substituted hydrazine (Formula II) with an alkyl halide, allyl halide or phenylmethylhalide in the presence of a base in an inert or substantially inert solvent or mixture of solvents according to the following process:

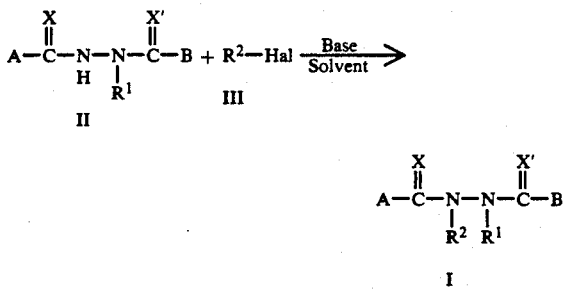

where X, X', $R^1$, $R^2$, A and B are as defined above for Formula I and Hal is halogen (chloro, fluoro or bromo).

Suitable bases for use in the above process include metal hydrides such as sodium hydride or potassium hydride; metal alkoxides such as sodium alkoxides or potassium alkoxides; sodium hydroxide; potassium hydroxide; or lithium diisopropyl amide. If desired, mixtures of these bases may be used. The preferred base is potassium t-butoxide.

Suitable solvents for use in the above process include ethers such as tetrahydrofuran (THF), glyme and the like; dimethylformamide (DMF); dimethylsulfoxide (DMSO); acetonitrile; or a mixture of water and benzene or toluene. If desired, mixtures of these solvents may be used. The preferred solvent is dimethylformamide.

The above process can be carried out at temperatures between about −20° C. and about 100° C. Preferably, this reaction is carried out between about −5° C. and about 50° C.

Preparation of the compounds of the present invention by the above process is preferably carried out at about atmospheric pressure although higher or lower pressures can be used if desired.

Substantially equimolar amounts of reactants are preferably used although higher or lower amounts can be used if desired.

Generally one equivalent of base is used per equivalent of starting material of Formula III.

The compounds of Formula III are generally commercially available or can be prepared by known procedures.

Modifications to the above process may be necessary to accommodate reactive functionalities of particular substituents. Such modifications would be apparent and known to those skilled in the art.

The compounds of Formula II or their precursors can be prepared according to the following processes. Process A can be used when preparing compounds according to Formula II where X and X' are both oxygen and A and B are the same (for example, both A and B are phenyl or 4-chlorophenyl) or different (for example, A is 4-methylphenyl and B is 4-bromophenyl).

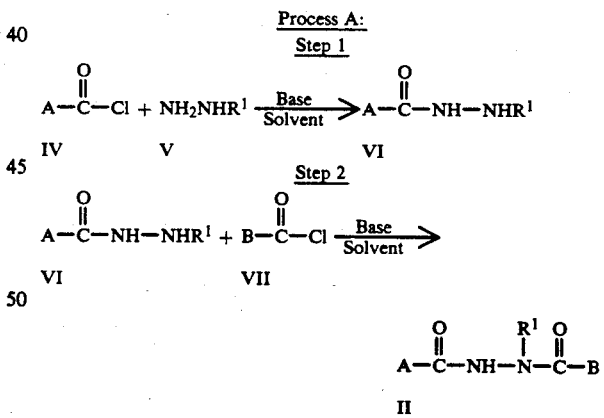

where $R^1$, A and B are as defined above for Formula I and X and X' are oxygen.

Process B can be used when preparing compounds according to Formula II where X and X' are oxygen, and $R^1$, A and B are as defined above for Formula I.

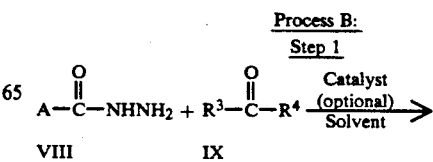

-continued
Process B:

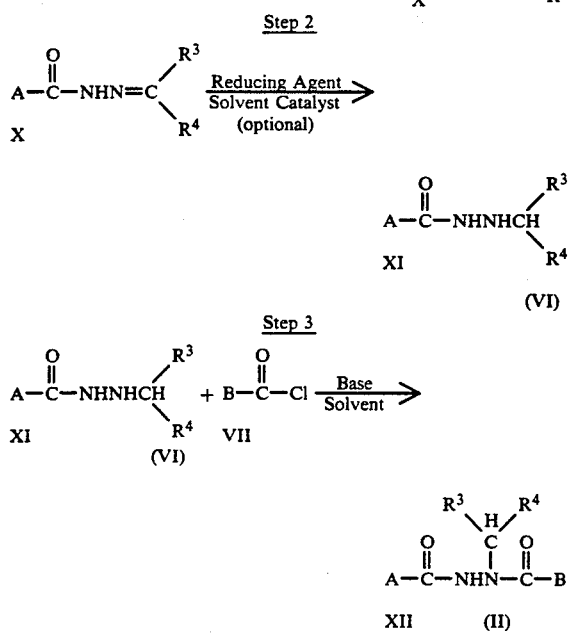

where X and X' are oxygen, A and B are as defined above for Formula I, and $R^3$ and $R^4$ are the same or different hydrogen or $(C_2-C_9)$ straight or branched chain unsubstituted or substituted alkyl have one or two of the same or different $(C_3-C_6)$cycloalkyl provided that $R^3$ and $R^4$ are not both H or $R^3$ or $R^4$ is not a straight chain alkyl group when the other ($R^3$ or $R^4$) is hydrogen. As can be seen above, the intermediate product of Step 2, the compounds of Formula XI, corresponds to the compounds of Formula VI. In addition, the compound of Formula XII corresponds to the compounds of Formula II where X and X' are oxygen.

Process C can be used when preparing compounds according to Formula I where A, B and $R^1$ are as defined for Formula I and one or both X and X' are sulfur.

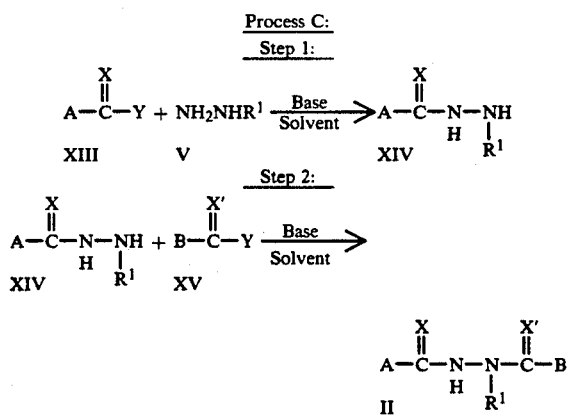

where A, B and $R^1$ are as defined above for Formula I and one or both X and X' are sulfur, and Y is a good leaving group such as carboxyalkylthio (for example, carboxymethylthio, $-SCH_2CO_2H$); alkylthio (for example, methylthio); or halo (for example, chloro).

In process A, a compound of Formula IV is reacted with a monosubstituted hydrazine of Formula V or a corresponding acid addition salt such as the hydrochloride salt or the like in the presence of a base in an inert or substantially inert solvent or mixture of solvents to afford an intermediate product of Formula VI which can be isolated or further reacted with a compound of Formula VII in the presence of a base in an inert or substantially inert solvent or mixture of solvents to afford the compounds of Formula II.

When A and B are the same, for example, both A and B are 4-chlorophenyl, two equivalents of a compound of Formula IV or VII are reacted with a monosubstituted hydrazine of Formula V in the presence of a base in an inert or substantially inert solvent or mixture of solvents to afford the compounds of Formula II.

Examples of the compounds of Formula IV and/or Formula VII which can be used in the above processes include benzoyl chloride, 4-chlorobenzoyl chloride, 4-methylbenzoyl chloride, 3,5-dichlorobenzoyl chloride, 2-bromobenzoyl chloride, 3-cyanobenzoyl chloride and the like. The compounds of Formula IV and/or Formula VII are generally commercially available or can be prepared by known procedures.

Examples of the compounds of Formula V which can be used in the above processes include isopropylhydrazine, t-butylhydrazine, neopentylhydrazine, alpha-methylneopentylhydrazine, isobutylhydrazine, isopentylhydrazine, isooctylhydrazine, and the like. The compounds of Formula V are generally commercially available or can be prepared by known procedures.

Suitable solvents for use in the above processes include water; alcohols such as methanol, ethanol, isopropanol and the like; hydrocarbons such as toluene, xylene, hexane, heptane and the like; glyme; tetrahydrofuran; acetonitrile; pyridine; or haloalkanes such as methylene chloride or mixtures of these solvents.

Preferred solvents are water, toluene, methylene chloride or a mixture of these solvents.

Examples of bases for use in the above processes include tertiary amines such as triethylamine; pyridine; potassium carbonate; sodium carbonate; sodium bicarbonate; sodium hydroxide; or potassium hydroxide. Preferred bases are sodium hydroxide, potassium hydroxide or triethylamine.

In Process B, a compound of Formula VIII is reacted with a ketone or aldehyde of Formula IX in an inert or substantially inert solvent or mixture of solvents and optionally in the presence of a catalyst to afford aN intermediate product of Formula X. The intermediate product of Formula X is then further reacted with a reducing agent in an inert or substantially inert solvent or mixture of solvents to afford a second intermediate product of Formula XI (VI) which can be isolated or further reacted with a compound of Formula VII in the presence of a base in an inert or substantially inert solvent or mixture of solvents to afford the compound of Formula II.

Examples of the compounds of Formula VIII which can be used in the above Process B include benzoylhydrazine, 4-chlorobenzoylhydrazine, 2-methylbenzoylhydrazine, 4-methylbenzoylhydrazine, 3,5-dichlorobenzoylhydrazine and the like. The compounds of Formula VIII are generally commercially available or can be prepared by known procedures.

Examples of the compounds of Formula IX which can be used in the above Process B include 1,1,1-trimethylacetaldehyde, methylethylketone, diethylketone and the like. The compounds of Formula IX are generally commercially available or can be prepared by known procedures.

Optionally, a catalyst may be used in Step 1 of Process B. Suitable catalysts generally include organic acids such as acetic acid, trifluoroacetic acid, oxalic acid and the like; mineral acids such as hydrochloric acid, sulfuric acid, nitric acid and the like; arylsulfonic acids such as toluenesulfonic acid; or pyridinium toluenesulfonate. Preferred catalysts are organic acids or arysulfonic acids. Most preferred catalysts are acetic acid or trifluoroacetic acid.

Suitable solvents for use in the above Process B, Step 1, include alcohols such as methanol, ethanol, isopropanol and the like; hydrocarbons such as toluene, benzene; ethers such as tetrahydrofuran (THF), glyme and the like; or dimethylformamide. Preferred solvents are alcohols and hydrocarbons. Most preferred solvents are alcohols such as methanol or ethanol.

Examples of suitable reducing agents for use in the above Process B, Step 2, include hydrides such as sodium borohydride and derivatives thereof such as sodium cyanoborohydride, lithium aluminum hydride and derivatives thereof and the like; or diborane. Preferred reducing agents are sodium borohydride and derivatives thereof or lithium aluminum hydride and derivatives thereof. Most preferred as a reducing agent is sodium cyanoborohydride.

Optionally, in Process B, Step 2, a catalyst may be included. Examples of suitable catalysts include organic acids such as acetic acid, trifluoroacetic acid; or mineral acids such as hydrochloric acid, sulfuric acid and the like. Preferred catalysts are organic acids or hydrochloric acid. Most preferred catalysts are acetic acid, trifluoroacetic acid or hydrochloric acid.

Suitable solvents for use in the above Process B, Step 2, include alcohols such as methanol, ethanol, isopropanol and the like; ethers such as tetrahydrofuran (THF), diethylether, glyme and the like; or halohydrocarbons such as methylene chloride, chloroform and the like. Preferred solvents are alcohols and most preferred are methanol or ethanol.

Step 3 of Process B corresponds to Step 2 of Process A. Consequently, those bases and solvents suitable for use in Step 2 of Process A are suitable for use in Step 3 of Process B including the preferred bases and solvents described above.

In Process C, a compound of Formula XIII is reacted with a monosubstituted hydrazine of Formula V or a corresponding acid addition salt such as the hydrochloride salt or the like in the presence of a base in an inert or substantially inert solvent or mixture of solvents to afford an intermediate compound of Formula XIV which can be isolated or further reacted with a compound of Formula XV in the presence of a base in an inert or substantially inert solvent or mixture of solvents to afford the desired product of Formula II.

When A and B are the same, for example, both A and B are unsubstituted phenyl, two equivalents of a compound Formula XIII or XV are reacted with a monosubstituted hydrazine of Formula III in the presence of a base in an inert or substantially inert solvent or mixture of solvents to afford the desired product of Formula II.

Examples of the compounds of Formula XIII and/or Formula XV which can be used in the above Process C include 3-methyl-methylthio-thiobenzoate, 4-chloromethylthio-thiobenzoate, 4-methyl-methylthio-thiobenzoate, carboxymethylthio-thiobenzoate and the like. The compounds of Formula XIII and/or Formula XV are generally commercially available or can be prepared by known procedures.

Suitable solvents for use in the above Process C are generally polar high-boiling solvents such as dimethylformamide (DMF); glyme; tetrahydrofuran (THF); and pyridine. The preferred solvent is pyridine.

Suitable bases for use in the above Process C include tertiary amines such as triethylamine; and pyridine. The preferred base is pyridine.

The above processes A and B can be carried out at temperatures between about $-20°$ C. and about $100°$ C. Preferably, these reactions are carried out between about $-5°$ C. and about $50°$ C.

Process C can be carried out at temperatures between about $10°$ C. and $200°$ C. Preferably, this reaction is carried out between about $70°$ C. and about $100°$ C.

Preparation of the compounds of the present invention by processes A, B and C is generally carried out at about atmospheric pressure, although higher or lower amounts can be used if desired.

Substantially equimolar amounts of reactants are preferably used in processes A, B and C, although higher or lower amounts can be used if desired.

Generally, when preparing the compounds of Formula II, about one equivalent of base is used per equivalent of starting material of Formula IV, VII, XIII and/or XV. Where the acid addition salt of the monosubstituted hydrazine of Formula V is used, one additional equivalent of base is used. For example, in Process A, when substituents A and B are the same and a monosubstituted hydrazine is used, about two equivalents of base are used since about two equivalents of a suitably substituted benzoyl chloride of Formula IV or VII are employed. In Process A, when substituents A and B are different and an acid addition salt of the monosubstituted hydrazine of Formula V is used, about two equivalents of base are used in Step 1 and about one equivalent of base is used in Step 2.

Modifications to the above processes may be necessary to accommodate reactive functionalities of particular A and/or B substituents. Such modifications would be apparent and known to those skilled in the art.

Alternatively, the compounds of the invention or their precursors can be prepared by substantially following the procedures described above for Process A except a disubstituted hydrazine $NH(R^2)NH(R^1)$ (Formula XVI) where $R^1$ and $R^2$ are as defined above for Formula I is employed rather than the monosubstituted hydrazine of Formula V.

The disubstituted hydrazines of Formula XVI are generally commercially available or can be prepared by known procedures. Those bases and solvents suitable for use in Process A are suitable for use in this alternative process including the preferred bases and solvents described. Substantially the same temperatures, pressures and amounts of materials are used, as described above for Process A.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more hydroxy or carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme and the like; dioxane; tetrahydrofuran; alcohols such as methanol, ethanol, isopropanol and the like. When metal hydrides are used as reagents, useful solvents include nonhydroxylic solvents, for example, ethers such as dioxane, glyme, diethylether and the like; tetrahydrofuran; hydrocarbons such as toluene, xylene, hexane, pentane, heptane, octane and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like. When the ammonium salt is other than a hydroxide or alkoxide, and additional base, such as potassium or sodium hydroxide, hydride, or alkoxide is generally used. The particular choice of solvent will depend on the relative solubilities of the starting material and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound of Formula I having a basic functional group in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out at from about −10° C. to about 100° C., preferably at about room temperature.

The following examples will further illustrate this invention but are not intended to limit it in any way. In Table I, some N-substituted-N'-substituted-N,N'-diacylhydrazines of the present invention that have been made are listed. Structures were confirmed by NMR and in some cases by IR and/or elemental analysis. Specific illustrative preparation of the compounds of Examples 1, 2, 3, 4, 5 and 8 are described after Table I.

TABLE I $$\begin{array}{c} X \quad\quad X \\ \| \quad\quad \| \\ A-C-N-N-C-B \\ | \quad | \\ R^2 \;\; R^1 \end{array}$$

| Ex. No. | X | X' | $R^1$ | $R^2$ | A | B |
|---|---|---|---|---|---|---|
| 1 | 0 | 0 | —C(CH$_3$)$_3$ | CH$_3$ | C$_6$H$_5$ | C$_6$H$_5$ |
| 2 | 0 | 0 | —C(CH$_3$)$_3$ | —CH$_2$C$_6$H$_5$ | C$_6$H$_5$ | C$_6$H$_5$ |
| 3 | 0 | 0 | —C(CH$_3$)$_3$ | —CH$_2$CH=CH$_2$ | C$_6$H$_5$ | C$_6$H$_5$ |
| 4 | 0 | 0 | —C(CH$_3$)$_3$ | —CH$_2$OCH$_3$ | C$_6$H$_5$ | C$_6$H$_5$ |
| 5 | 0 | 0 | —C(CH$_3$)$_3$ | —CH$_2$SCH$_3$ | C$_6$H$_5$ | C$_6$H$_5$ |
| 6 | 0 | 0 | —C(CH$_3$)$_3$ | —CH$_2$C≡CH | C$_6$H$_5$ | C$_6$H$_5$ |
| 7 | 0 | 0 | —C(CH$_3$)$_3$ | —CH$_2$C≡CH | C$_6$H$_4$CH$_3$-4 | C$_6$H$_4$CH$_3$-3 |
| 8 | 0 | 0 | —C(CH$_3$)$_3$ | —CH$_2$C≡CH | C$_6$H$_5$ | C$_6$H$_3$(CH$_3$)$_2$-3,5 |
| 9 | 0 | 0 | —C(CH$_3$)$_3$ | —CH$_2$C≡CH | C$_6$H$_5$ | C$_6$H$_3$Cl$_2$-2,4 |
| 10 | 0 | 0 | —C(CH$_3$)$_3$ | —CH$_2$C≡CH | C$_6$H$_5$ | C$_6$H$_3$Cl$_2$-3,4 |
| 11 | 0 | 0 | —C(CH$_3$)$_3$ | —CH$_2$C$_6$H$_4$Br-4 | C$_6$H$_5$ | C$_6$H$_5$ |

EXAMPLE NO. 1

Preparation of N-methyl-N'-t-butyl-N,N'-dibenzoylhydrazine

To a stirred solution of N'-t-butyl-N,N'-dibenzoylhydrazine (2.5 g, 0.008M) in dimethylformamide (DMF) (30 ml) at room temperature under nitrogen was added portionwise sodium hydride (60% oil dispersion) (0.4 g, 0.009M). The mixture was stirred at room temperature for 0.5 hours, and then methyl iodide (1.0 g, 0.008M) was added dropwise. The reaction mixture was allowed to stir for 1 hour. The mixture was then diluted with water (50 ml), neutralized with 10% HCl, and the product extracted into methylene chloride (50 ml). The methylene chloride layer was washed with water (5×20 ml), dried over anhydrous magnesium sulfate, and the methylene chloride removed under vacuum to afford N-methyl-N'-t-butyl-N,N'-dibenzoylhydrazine as an oil.

EXAMPLE NO. 2

Preparation of N-benzyl-N'-t-butyl-N,N'-dibenzoylhydrazine

To a stirred solution of N'-t-butyl-N,N'-dibenzoylhydrazine (2 g, 0.006M) in DMF (25 ml) at room temperature under nitrogen was added portionwise sodium hydride (60% oil dispersion) (0.3 g, 0.007M). The mixture was stirred at room temperature for 0.5 hours, and thenbenzyl bromide (1.2 g, 0.007M) was added dropwise. The reaction mixture was warmed to 60° C. and allowed to stir for 2 hours. The mixture was then diluted with water (50 ml), neutralized with 1% HCl, and the product extracted into methylene chloride (50 ml). The methylene chloride layer was washed with water (5×20 ml), dried over anhydrous magnesium sulfate, and the methylene chloride removed under vacuum to afford N-benzyl-N'-t-butyl-N,N'-dibenzoylhydrazine as an oil.

EXAMPLE NO. 3

Preparation of N-allyl-N'-t-butyl-N,N'-dibenzoylhydrazine

To a stirred solution of N'-t-butyl-N,N'-dibenzoylhydrazine (3 g, 0.011M) in DMF (30 ml) at room temperature under nitrogen was added portionwise sodium hydride (60% oil dispersion) (0.5 g, 0.012M). The mixture was stirred at room temperature for 0.5 hours, and then allyl iodide (1.8 g, 0.01M) was added dropwise. The reaction mixture was warmed to 60° C. and stirred for 2 hours. The mixture was then diluted with water (50 ml), neutralized with 10% HCl, and the product extracted into methylene chloride (50 ml). The methylene chloride layer was washed with water (5×20 ml), dried over anhydrous magnesium sulfate, and the methylene chloride removed under vacuum to afford N-allyl-N'-t-butyl-N,N'-dibenzoylhydrazine as an oil.

EXAMPLE NO. 4

Preparation of N-methoxymethyl-N'-t-butyl-N-N'-dibenzoylhydrazine

N'-t-butyl-N,N'-dibenzoylhydrazine (2 g, 0.007M) was stirred at room temperature in a two phase system of toluene-50% sodium hydroxide with 100 mg of phase transfer catalyst (tetra-n-butylammonium hydrogen sulfate). Methoxymethyl chloride (1.2 g, 0.015M) was added dropwise and the mixture was stirred 3 hours. The layers were separated and the toluene layer was washed several times with water (until the water washes were neutral). The toluene solution was dried over anhydrous magnesium sulfate and the toluene removed under vacuum to afford N-methoxymethyl-N'-t-butyl-N,N'-dibenzoylhydrazine as a thick oil.

EXAMPLE NO. 5

Preparation of N-methylthiomethyl-N'-t-butyl-N,N'-dibenzoylhydrazine

To a stirred suspension of sodium hydride (a 50% oil dispersion washed 2 times with 20 ml pentane) (0.21 g, 0.0043M) in dry DMF (20 ml) under nitrogen at room temperature, was added N'-t-butyl-N,N'-dibenzoylhydrazine (1 g, 0.0034M) portionwise as a solid. The mixture was stirred at room temperature for ½ hour and methylthiomethylchloride (0.34 g, 0.0035M) was added dropwise. The resulting mixture was heated at 50° C. overnight, cooled, diluted with methylene chloride and washed repeatedly with water. The organic layer was dried over anhydrous magnesium sulfate and the methylene chloride removed under vacuum. The oily residue was chromatographed on silica gel using methylene chloride to afford N-methylthiomethyl-N'-t-butyl-N,N'-dibenzoylhydrazine as an oil (60% yield).

EXAMPLE NO. 8

Preparation of N-(2-propynyl)-N'-t-butyl-N-benzoyl-N'-(3,5-dimethylbenzoyl)hydrazine To a stirred suspension of N'-t-butyl-N-benzoyl-N'-(3,5-dimethylbenzoyl)hydrazine (1.5 g) in dimethylformamide (DMF) (20 ml) was added sodium hydride (200 mg of 60% oil dispersion) portionwise. After 15 min., propargyl bromide (0.6 g) was added to the reaction mixture dropwise and the reaction stirred for 1 hour. The reaction mixture was diluted with ethyl acetate (50 ml) and washed with water (5×20 ml). The organic layer was then dried over magnesium sulfate and the solvent removed under vacuum to afford N-(2-propynyl)-N'-t-butyl-N-benzoyl-N'-(3,5-dimethylbenzoyl)hydrazine as a yellow amorphous solid. The product, N-(2-propynyl)-N'-t-butyl-N-benzoyl-N'-(3,5-dimethylbenzoyl)hydrazine, was purified by column chromatography on silica gel (solvent system: methylene chloride) to afford a 70% yield as a white solid.

By following substantially the processes for preparing the compounds of the present invention as described above and as exemplified by the illustrative preparation of the compounds of Examples 1, 2, 3, 4, 5 and 8, the compounds of Formula I are prepared.

As previously noted, the compounds of the present invention exhibit excellent insecticidal activity and are selective against insects of the orders Lepidoptera and Coleoptera.

In general, for the control of insects in agriculture, horticulture and forestry, a dosage corresponding to from about 10 grams to about 10 kilograms of the active substance per hectare may be used and from about 100 grams to about 5 kilograms per hectare of the active substance is preferred. The exact amount of dosage for a given situation can be routinely determined and depends on a variety of factors, for example, the substance used, the kind of pest, the formulation used, the state of the crop infested with the pest and the prevailing weather conditions. The term "insecticidal" as employed in the specification and claims of this application is to be construed as any means which adversely affects the existence or growth of the target insects. Such means can comprise a complete killing action, eradication, arresting in growth, inhibition, reducing in number or any combination thereof. The term "control" as employed in the specification and claims of this application is to be construed as meaning "insecticidal" or protecting plants from insect damage. By "insecticidally active amount" is meant that dosage of active substance sufficient to exert insect "control."

The compounds of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973), edited by Wade Van Valkenburg. In these compositions and formulations, the active substance is mixed with conventional inert agronomically acceptable (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, adjuvants such as surfactants, stabilizers, antifoam agents and antidrift agents may also be added.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior, feeding habits and physiology of the pest for the purpose of control.

The invert emulsions are mainly used for aerial application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cottonseed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or nonionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolysates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is present in an amount substantially between about 0.0001% and 5%, preferably between about 0.001% and 3%, by weight of the mixture. Thus the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant (e.g., a surface-active agent, such as an emulsifying agent and/or a dispersing agent), and an amount of the active compound, generally between about 0.0001% and about 99% by weight of the composition, preferably between about 0.001% and about 90% by weight of the composition, and more preferably between about 0.01% and about 75% by weight of the composition, which is effective for the purpose in question.

The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of selectively killing, combatting or controlling pests, which comprises contacting insects with a correspondingly combative or toxic amount (i.e., an insecticidally effective amount) of at least one active compound of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example, to a growing crop or an area where a crop is to be grown), the active compound of this invention alone or as a constituent of a conmposition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example, pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such as, for example, ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance, optionally dissolved in a volatile solvent such as acetone, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight depending upon toxicant solubility. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e., preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients, the preparations according to the invention may also contain other substances commonly used in preparations of this kind.

For example, a lubricant, such as calcium stearate or magnesium stearate, may be added to a wettable powder or to a mixture to be granulated. Furthermore, there may, for example, be added "adhesives" such as polyvinylalcohol cellulose derivatives or other colloidal materials, such as casein, to improve the adherence of this pesticide to the surface to be protected.

Representative preparation of compositions and formulations including the compounds of the present invention are set forth below as Examples A through I by way of illustration but not limitation.

EXAMPLE A

Granular

| Ingredient | %/wt. |
|---|---|
| Toxicant and toxicant impurities | 0.25 |
| Triton ® X-305 (binder) (Octylphenyl-30-ethylene oxide ethanol) | 0.25 |
| Agsorb ® 24/48 (diluent) (Montmorillonite clay) | 99.50 |

Preparation: The toxicant and Triton ® X-305 are dissolved into methylene chloride and the mixture is added to the Agsorb ® with continuous mixing. The methylene chloride is then allowed to evaporate.

EXAMPLE B

Dust

| Ingredient | %/wt. |
|---|---|
| Toxicant and toxicant impurities | 1.0 |
| Talc | 99.0 |

Preparation: Toxicant is dissolved in excess acetone and the mixture is impregnated onto the talc. The acetone is then permitted to evaporate.

EXAMPLE C

Wettable Powder

| Ingredient | %/wt. |
|---|---|
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| Barden clay (diluent) | 31.7 |
| HiSil ® 233 (diluent) (Sodium silica) | 30.0 |

Preparation: The toxicant optionally dissolved in a volatile solvent is absorbed onto the Barden clay and HiSil ® carriers. The Duponal ® and Reax ® are then added and the entire dry mixture blended until homogeneous. The composition is then micronized to a fine particle size.

EXAMPLE D

Emulsifiable Concentrate

| Ingredient | %/wt. |
|---|---|
| Toxicant and toxicant impurities | 15.0 |
| Sponto ® 232T (emulsifier) (Anionic and nonionic blend of the following surfactants: calcium dodecyl benzene sulfonate; and ethoxylated alkylphenol) | 6.0 |
| Sponto ® 234T (emulsifier) (Anionic and nonionic blend of the following surfactants: calcium dodecyl benzene sulfonate; and ethoxylated alkylphenol) | 4.0 |
| Cyclohexanone (solvent) | 22.5 |
| Tenneco ® 500-100 (solvent) (Aromatic solvent mixture principally comprising xylene, cumene and ethyl benzene having a boiling point range of 290–345° F.) | 52.5 |

Preparation: All ingredients are mixed together with continuous agitation until a homogenous clear solution is obtained.

EXAMPLE E

Aerosol

| Ingredient | %/wt. |
|---|---|
| Toxicant and toxicant impurities | 0.5 |
| Freon 12 | 99.5 |

Preparation: The components are mixed and packaged under pressure in a suitable container equipped with a release spray valve.

EXAMPLE F

Fumigating Candle or Fumigating Powder

| Ingredient | %/wt. |
|---|---|
| Toxicant and toxicant impurities | 1.0 |
| Wood dust | 96.0 |
| Starch | 3.0 |

Preparation: Toxicant, wood dust, and starch are blended together and then molded into a candle using a small amount of water to activate the starch.

EXAMPLE G

Bait

| Method A | |
|---|---|
| Ingredient | %/wt. |
| Toxicant and toxicant impurities | 1.00 |
| Wheat Bran (carrier and attractant) | 89.95 |
| Corn syrup (attractant) | 7.00 |
| Corn Oil (attractant) | 2.00 |
| Kathon ® 4200 (preservative) (3-isothiazolone) | 0.05 |

Preparation: The corn oil and corn syrup are added to the wheat bran with adequate mixing. The toxicant and Kathon ® are premixed with excess acetone and this solution is added to the wheat bran base with continued mixing. The acetone is then permitted to evaporate.

| Method B | |
|---|---|
| Ingredient | %/wt. |
| Toxicant and toxicant impurities | 0.06 |
| Granulated Sugar (carrier and attractant) | 99.94 |

EXAMPLE H

Pellet

Same as Example G, Method A, with this addition: the bait composition is formed into ¼" diameter by ⅜" long pellets using a suitable die and press apparatus.

EXAMPLE I

Flowable

| Ingredient | %/wt. |
|---|---|
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| HiSil ® 233 (diluent) (Sodium silica) | 30.0 |
| Kelzan ® (thickener) (Xanthan gum) | 0.5 |
| Water | 31.2 |

Preparation: The toxicant is absorbed onto the HiSil ® carrier. The Duponal ® and Reax ® are then added and the entire dry mixture blended until homogeneous. The composition is then micronized to a fine particle size. The resulting powder is suspended in water and the Kelzan ® added.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation.

Insecticides such as:

Chlorinated hydrocarbons, for example, 2,2bis(p-chlorophenyl)-1,1,1-trichloroethane and hexachloroepoxyoctahydrodimethanonaphthalene;

Carbamates, for example, N-methyl-1-naphthylcarbamate;

Dinitrophenols, for example, 2-methyl-4,6-dinitrophenol and 2-(2-butyl)-4,6-dinitrophenyl-3,3-dimethylacrylate;

Organic phosphorus compounds, such as dimethyl-2-methoxy-3-carbonyl-1-methylvinyl phosphate, 0,0-diethyl-0-p-nitrophenylphosphorothioate; N-monomethylamide of 0,0-dimethyldithiophosphorylacetic acid;

Diphenylsulfides, for example, p-chlorobenzyl or p-chlorophenyl sulfide and 2,4,4', 5-tetrachlorodiphenylsulfide;

Diphenylsulfonates, for example, p-chlorophenylbenzenesulfonate;

Methylcarbinols, for example, 4,4-dichloro-1-trichloromethylbenzhydrol;

Quinoxaline compounds, such as methylquinoxaline dithiocarbobate;

Amidines such as N'-(4-chloro-2-methylphenyl) N,N-dimethylformamidine;

Pyrethroids such as Allethrin;

Biologicals such as *Bacillus thuringiensis preparations;*

Organic tin compounds such as tricyclohexyltin hydroxide;

Synergists such as piperonyl butoxide.

Fungicides such as:

Organic mercury compounds, for example, phenylmercuryacetate and methylmercurycyanoguanide;

Organic tin compounds, for example, triphenyltin hydroxide and triphenyltin acetate;

Alkylenebisdithiocarbamates, for example, zinc ethylenebisthiocarbamate and manganese ethylenebisdithiocarbamate; and 2,4-dinitro-6-(2-octyl-phenylcrotonate), 1-bis(dimethylamino)phosphoryl-3-phenyl-5-amino-1,2,4-triazole, 6-methylquinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

Biological Activity

It has been found by biological evaluation that compounds according to the present invention have pesticidal activity and are capable of controlling larvae and adult forms of pests, especially insects from the orders Lepidoptera and Coleoptera and most particularly insects from the order Lepidoptera. One skilled in the art will know how to determine the activity of a given compound against a given insect and the dosage required to obtain general or selective insecticidal effects.

As previously noted, the compounds of the present invention are particularly suitable for controlling plant-destructive insects in crops of cultivated plants, such as, but not limited to, cotton, vegetables, corn and other cereals and the like; forestry, such as, but not limited to, birch, spruce, pine, fir and the like; and ornamental plants, flowers and trees. Compounds of the present invention are also particularly suitable for controlling insects destructive to stored commodities such as seeds and the like; fruit crops, such as, but not limited to, fruit and/or citrus trees, raspberry bushes and the like; and turf, such as, but not limited to, lawns, sod and the like.

In evaluating the pesticidal activity of the compounds of this invention, the following test procedures were employed.

A test solution containing 600 parts per million (ppm) was made by dissolving the test compound in a solvent (acetone:methanol, 1:1), adding water to give an acetone:methanol:water system of 5:5:90 and then a surfactant. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

Initial evaluations were made on one or more of the following pests:

| Code Symbol | Common Name | Latin Name |
| --- | --- | --- |
| SAW | Southern Armyworm | *Spodoptera eridania* |
| MBB | Mexican Bean Beetle | *Epilachna varivestis* |

For the foliar bean beetle and armyworm tests, individual bean (*Phaseolus limensis* var. Woods' Prolific) leaves are placed on moistened pieces of filter paper in Petri dishes. The leaves are then sprayed with the test solution using a rotating turntable and allowed to dry. The dishes are infested with 10 third instar larvae of Southern armyworm or Mexican bean beetle. The dishes are then covered.

The percent mortality for the bean beetle and armyworm evaluations are determined 96 hours after treatment. Evaluations are based on a scale of 0-100% in which 0 equals no activity and 100 equals total kill.

The rotating turntable consists of a fixed, continuously operating spray nozzle under which targets are rotated at a fixed speed and distance. When the target is a Petri dish (such as for the armyworm), the distance from the nozzle is 15 inches. The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig air pressure used and with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

All treatments are maintained at 75°-80° F. under continuous fluorescent light in a well-ventilated room.

The results of the initial insecticidal evaluations are given in Table II.

Armyworm and bean beetle spray (foliar) results are 96 hour observations unless otherwise noted.

TABLE II

| | Initial Biological Evaluations | |
|---|---|---|
| | Foliar Application Test Species | |
| Example No. | SAW | MBB |
| 1 | 0 | 100 |
| 2 | 0 | 100 |
| 3 | 100 | 100 |
| 4 | 100 | 10 |
| 5 | 10 | 20 |
| 6 | 100 | 80 |
| 7 | 100 | 30 |
| 8 | 100 | 100 |
| 9 | 100 | 20 |
| 10 | 100 | 40 |
| 11 | 100 | 20 |

It should be understood that the instant specification and examples are set forth by way of illustration and not limitation, and that various modifications and changes may be made without departing from the spirit and scope of the present invention as defined by the appended claims.

We claim:

1. A compound of the formula

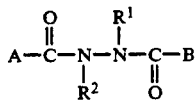

wherein

R$^1$ is branched (C$_4$-C$_7$)alkyl containing a tertiary carbon;

R$^2$ is (C$_1$-C$_4$)alkyl, (C$_1$-C$_4$)alkoxy(C$_1$-C$_4$)alkyl, (C$_1$-C$_4$)alkylthio(C$_1$-C$_4$)alkyl, (C$_2$-C$_5$)alkenyl, (C$_2$-C$_5$)alkynyl, phenyl(C$_1$-C$_4$)alkyl or halophenyl(C$_1$-C$_4$)alkyl; and A and B are the same or different naphthyl or phenyl; wherein phenyl is optionally substituted by from one to five of the same or different halo or by from one to three of the same or different nitro, hydroxy, (C$_1$-C$_6$)alkyl, (C$_1$-C$_6$)haloalkyl, (C$_1$-C$_6$)alkoxy, halo(C$_1$-C$_6$)alkoxy, (C$_1$-C$_6$)alkoxy(C$_1$-C$_6$)alkoxy, (C$_2$-C$_6$)alkenyl, halo(C$_2$-C$_6$)alkenyl, (C$_2$-C$_6$)alkynyl, (C$_1$-C$_6$)alkanoyl, amino, (C$_1$-C$_6$)alkylamino, di(C$_1$-C$_6$)alkylamino, (C$_1$-C$_6$)alkylcarbonylamino, phenyl or phenyloxy; and agronomically acceptable salts thereof.

2. The compound of claim 1 wherein

R$^1$ is t-butyl, 2,2-dimethylpropyl or 1,2,2-trimethylpropyl;

R$^2$ is (C$_1$-C$_4$)alkyl, (C$_1$-C$_4$)alkoxy(C$_1$-C$_4$)alkyl, (C$_1$-C$_4$)alkylthio(C$_1$-C$_4$)alkyl, (C$_2$-C$_4$)alkenyl, (C$_2$-C$_4$)alkynyl, phenyl(C$_1$-C$_4$)alkyl or halophenyl(C$_1$-C$_4$)alkyl;

A and B are independently phenyl optionally substituted with from one to three of the same or different halo, nitro, (C$_1$-C$_4$)alkyl, (C$_1$-C$_4$)alkoxy, or halo(C$_1$-C$_4$)alkyl.

3. The compound of claim 2 wherein R$^1$ butyl.

4. The compound of claim 3 wherein R$^2$ is methyl, methoxymethyl, methylthiomethyl, allyl.

5. The compound of claim 4 wherein A and B are unsubstituted phenyl or phenyl substituted by one or two of the same or different halo, (C$_1$-C$_4$)alkyl, halo(C$_1$-C$_4$)alkyl or (C$_1$-C$_4$)alkoxy.

6. The compound of claim 5 wherein R$^2$ is 2-propynyl and A and B are unsubstituted phenyl or phenyl substituted by one or two of the same different bromo, chloro, fluoro, iodo, methyl, ethyl, methoxy or trifluoromethyl.

7. The compound of claim 6 wherein A is 4-methylphenyl and B is 3-methylphenyl.

8. The compound of claim 6 wherein A is phenyl and B is phenyl.

9. The compound of claim 6 wherein A is phenyl and B is 2,4-dichlorophenyl.

10. The compound of claim 6 wherein A is phenyl and B is 3,4-dichlorophenyl.

11. An insecticidal composition which comprises an agronomically acceptable carrier and an insecticidally effective amount of the compound of claim 1.

12. An insecticidal composition which comprises an agronomically acceptable carrier and an insecticidally effective amount of the compound of claim 2.

13. An insecticidal composition which comprises an agronomically acceptable carrier and an insecticidally effective amount of the compound of claim 3.

14. An insecticidal composition which comprises an agronomically acceptable carrier and an insecticidally effective amount of the compound of claim 4.

15. An insecticidal composition which comprises an agronomically acceptable carrier and an insecticidally effective amount of the compound of claim 5.

16. An insecticidal composition which comprises an agronomically acceptable carrier and an insecticidally effective amount of the compound of claim 6.

17. The composition of claim 11 wherein the compound is present at from about 0.0001 to about 99% by weight of the composition.

18. The composition of claim 11 wherein the agronomically acceptable carrier is a solid.

19. The composition of claim 11 wherein the agronomically acceptable carrier is a liquid.

20. The composition of claim 11 which additionally contains an emulsifying agent, the composition being in the form of an emulsifiable concentrate.

21. The composition of claim 18 additionally containing a dispersing agent, the composition being in the form of a wettable powder.

22. The composition of claim 18 additionally containing a liquid agronomically acceptable carrier and a dispersing agent, the composition being in the form of a flowable solid.

23. The composition of claim 18 wherein the composition is in the form of a dust.

24. The composition of claim 18 additionally containing a binding agent, the composition being in the form of a granule.

25. The composition of claim 18 additionally containing an attractant agent, the composition being in the form of a bait.

26. The composition of claim 16 wherein the compound is N-(2-propynyl)-N'-t-butyl-N-(4-methylbenzoyl)-N'-(3-methylbenzoyl)hydrazine.

27. The composition of claim 16 wherein the compound the compound is N-(2-propynyl)-N'-t-butyl-N,N'-dibenzoylhydrazine.

28. The composition of claim 16 wherein the compound is N-(2-propynyl)-N'-t-butyl-N-benzoyl-N'-(2,4-dichlorobenzoyl)hydrazine.

29. The composition of claim 16 wherein the compound is N-(2-propynyl)-N'-t-butyl-N-benzoyl-N'-(3,4-dichlorobenzoyl)hydrazine.

* * * * *